US009636254B2

(12) United States Patent
Yu et al.

(10) Patent No.: US 9,636,254 B2
(45) Date of Patent: May 2, 2017

(54) SYSTEMS FOR REDUCING PRESSURE IN AN ORGAN

(75) Inventors: Dao-Yi Yu, City Beach (AU); Cory Anderson, Alpharetta, GA (US); Roelof Trip, Suwanee, GA (US); Ying Yang, Union City, CA (US); Hoang Van Nguyen, San Jose, CA (US); Surag Mantri, Sunnyvale, CA (US); Er-Ning Su, City Beach (AU); Stephen Cringle, Shenton Park (AU); James McCrea, Burlingame, CA (US); Daniel Mufson, Napa, CA (US); Colin Tan, Sunnyvale, CA (US)

(73) Assignee: AqueSys, Inc., Aliso Viejo, CA (US)

( * ) Notice: Subject to any disclaimer, the term of this patent is extended or adjusted under 35 U.S.C. 154(b) by 261 days.

(21) Appl. No.: 12/620,564

(22) Filed: Nov. 17, 2009

(65) Prior Publication Data

US 2010/0100104 A1    Apr. 22, 2010

Related U.S. Application Data

(63) Continuation of application No. 11/771,805, filed on Jun. 29, 2007, now abandoned.

(60) Provisional application No. 60/806,402, filed on Jun. 30, 2006.

(51) Int. Cl.
| | | |
|---|---|---|
| *A61F 9/007* | (2006.01) | |
| *A61L 31/04* | (2006.01) | |
| *A61M 27/00* | (2006.01) | |
| *A61F 9/00* | (2006.01) | |

(52) U.S. Cl.
CPC ........ *A61F 9/00781* (2013.01); *A61L 31/045* (2013.01); *A61M 27/008* (2013.01); *A61F 9/0008* (2013.01)

(58) Field of Classification Search
CPC .. A61F 9/00781; A61F 9/0017; A61F 9/0008; A61F 9/00772; A61F 9/007; A61M 5/3158
USPC ....... 606/107, 108, 153–155; 623/1.11, 6.12; 128/898
See application file for complete search history.

(56) References Cited

U.S. PATENT DOCUMENTS

| | | |
|---|---|---|
| 3,788,327 A | 1/1974 | Donowitz et al. |
| 3,960,150 A | 6/1976 | Hussain et al. |
| 4,090,530 A | 5/1978 | Lange |
| 4,402,308 A | 9/1983 | Scott |

(Continued)

FOREIGN PATENT DOCUMENTS

| | | |
|---|---|---|
| DE | 4310842 A1 | 10/1994 |
| GB | 2 296 663 A | 7/1996 |

(Continued)

OTHER PUBLICATIONS

International Search Report in PCT application No. PCT/US2007/072547, mailed May 23, 2008, 7 pages.

(Continued)

*Primary Examiner* — Katherine M Shi
*Assistant Examiner* — Michael Mendoza
(74) *Attorney, Agent, or Firm* — Nathan S. Smith; McDermott Will & Emery LLP

(57) ABSTRACT

Methods, system and apparatus for relieving pressure in an organ such as, but not limited to, the eye are disclosed. The method includes implanting a bioabsorbable channel into the selected area of the organ using a delivery apparatus.

40 Claims, 20 Drawing Sheets

(56) References Cited

U.S. PATENT DOCUMENTS

| | | |
|---|---|---|
| 4,562,463 A | 12/1985 | Lipton |
| 4,583,117 A | 4/1986 | Lipton et al. |
| 4,700,692 A | 10/1987 | Baumgartner |
| 4,722,724 A | 2/1988 | Schocket |
| 4,744,362 A | 5/1988 | Grundler |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,826,478 A | 5/1989 | Schocket |
| 4,836,201 A | 6/1989 | Patton et al. |
| 4,848,340 A | 7/1989 | Bille et al. |
| 4,863,457 A | 9/1989 | Lee |
| 4,902,292 A | 2/1990 | Joseph |
| 4,911,161 A | 3/1990 | Schechter |
| 4,915,684 A | 4/1990 | Mackeen et al. |
| 4,934,363 A | 6/1990 | Smith et al. |
| 4,936,825 A | 6/1990 | Ungerleider |
| 4,946,436 A | 8/1990 | Smith |
| 4,968,296 A | 11/1990 | Ritch et al. |
| 4,978,352 A | 12/1990 | Federov et al. |
| 5,041,081 A | 8/1991 | Odrich |
| 5,057,098 A | 10/1991 | Zelman |
| 5,071,408 A | 12/1991 | Ahmed |
| 5,092,837 A | 3/1992 | Ritch et al. |
| 5,098,426 A | 3/1992 | Sklar et al. |
| 5,098,443 A | 3/1992 | Parel et al. |
| 5,162,641 A | 11/1992 | Fountain |
| 5,178,604 A | 1/1993 | Baerveldt et al. |
| 5,180,362 A | 1/1993 | Worst |
| 5,201,750 A | 4/1993 | Hocherl et al. |
| 5,207,660 A | 5/1993 | Lincoln |
| 5,275,622 A | 1/1994 | Lazarus et al. |
| 5,290,295 A | 3/1994 | Querals et al. |
| 5,300,020 A | 4/1994 | L'Esperance, Jr. |
| 5,333,619 A | 8/1994 | Burgio |
| 5,338,291 A | 8/1994 | Speckman et al. |
| 5,342,370 A | 8/1994 | Simon et al. |
| 5,360,339 A | 11/1994 | Rosenberg |
| 5,368,015 A | 11/1994 | Wilk |
| 5,370,607 A | 12/1994 | Memmen |
| 5,399,951 A | 3/1995 | Lavallee et al. |
| 5,410,638 A | 4/1995 | Colgate et al. |
| 5,443,505 A | 8/1995 | Wong et al. |
| 5,476,445 A | 12/1995 | Baerveldt et al. |
| 5,516,522 A | 5/1996 | Peyman et al. |
| 5,520,631 A | 5/1996 | Nordquist et al. |
| 5,558,629 A | 9/1996 | Baerveldt et al. |
| 5,558,630 A | 9/1996 | Fisher |
| 5,601,094 A | 2/1997 | Reiss |
| 5,656,026 A | 8/1997 | Joseph |
| 5,665,093 A | 9/1997 | Atkins et al. |
| 5,665,114 A | 9/1997 | Weadock et al. |
| 5,670,161 A | 9/1997 | Healy et al. |
| 5,688,562 A | 11/1997 | Hsiung |
| 5,695,474 A | 12/1997 | Daugherty |
| 5,702,414 A | 12/1997 | Richter et al. |
| 5,704,907 A | 1/1998 | Nordquist et al. |
| 5,707,376 A | 1/1998 | Kavteladze et al. |
| 5,722,948 A | 3/1998 | Gross |
| 5,743,868 A | 4/1998 | Brown et al. |
| 5,763,491 A | 6/1998 | Brandt et al. |
| 5,868,697 A | 2/1999 | Richter et al. |
| 5,908,449 A | 6/1999 | Bruchman et al. |
| 5,932,299 A | 8/1999 | Katoot |
| 5,938,583 A | 8/1999 | Grimm |
| 5,968,058 A | 10/1999 | Richter et al. |
| 6,007,511 A | 12/1999 | Prywes |
| 6,007,578 A | 12/1999 | Schachar |
| 6,050,970 A | 4/2000 | Baerveldt |
| 6,086,543 A | 7/2000 | Anderson et al. |
| 6,102,045 A | 8/2000 | Nordquist et al. |
| 6,146,366 A | 11/2000 | Schachar |
| 6,165,210 A | 12/2000 | Lau et al. |
| 6,203,513 B1 | 3/2001 | Yaron et al. |
| 6,228,023 B1 | 5/2001 | Zaslavsky et al. |
| 6,228,873 B1 | 5/2001 | Brandt et al. |
| 6,261,256 B1 | 7/2001 | Ahmed |
| 6,264,665 B1 | 7/2001 | Yu et al. |
| 6,280,468 B1 | 8/2001 | Schachar |
| 6,413,540 B1 | 7/2002 | Yaacobi |
| 6,450,937 B1 | 9/2002 | Mercereau et al. |
| 6,450,984 B1 | 9/2002 | Lynch et al. |
| 6,464,724 B1 | 10/2002 | Lynch et al. |
| 6,468,283 B1 | 10/2002 | Richter et al. |
| 6,471,666 B1 | 10/2002 | Odrich |
| 6,483,930 B1 | 11/2002 | Musgrave et al. |
| 6,510,600 B2 | 1/2003 | Yaron et al. |
| 6,524,275 B1 | 2/2003 | Lynch et al. |
| 6,533,768 B1 | 3/2003 | Hill |
| 6,544,249 B1 | 4/2003 | Yu et al. |
| 6,558,342 B1 | 5/2003 | Yaron et al. |
| 6,595,945 B2 | 7/2003 | Brown |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,726,664 B2 | 4/2004 | Yaron et al. |
| D490,152 S | 5/2004 | Myall et al. |
| 6,736,791 B1 | 5/2004 | Tu et al. |
| 6,752,753 B1 | 6/2004 | Hoskins et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,936,053 B1 | 8/2005 | Weiss |
| 6,939,298 B2 | 9/2005 | Brown et al. |
| 6,955,656 B2 | 10/2005 | Bergheim et al. |
| 6,981,958 B1 | 1/2006 | Gharib et al. |
| 7,008,396 B1 | 3/2006 | Straub |
| 7,037,335 B2 | 5/2006 | Freeman et al. |
| 7,041,077 B2 | 5/2006 | Shields |
| 7,094,225 B2 | 8/2006 | Tu et al. |
| 7,118,547 B2 | 10/2006 | Dahan |
| 7,135,009 B2 | 11/2006 | Tu et al. |
| 7,163,543 B2 | 1/2007 | Smedley et al. |
| 7,186,232 B1 | 3/2007 | Smedley et al. |
| 7,207,980 B2 | 4/2007 | Christian et al. |
| 7,220,238 B2 | 5/2007 | Lynch et al. |
| 7,291,125 B2 | 11/2007 | Coroneo |
| 7,331,984 B2 | 2/2008 | Tu et al. |
| 7,431,710 B2 | 10/2008 | Tu et al. |
| 7,458,953 B2 | 12/2008 | Peyman |
| 7,488,303 B1 | 2/2009 | Haffner et al. |
| 7,563,241 B2 | 7/2009 | Tu et al. |
| 7,625,384 B2 | 12/2009 | Eriksson et al. |
| 7,708,711 B2 | 5/2010 | Tu et al. |
| 7,722,549 B2 | 5/2010 | Nakao |
| 7,867,186 B2 | 1/2011 | Haffner et al. |
| 7,879,001 B2 | 2/2011 | Haffner et al. |
| 8,308,701 B2 | 11/2012 | Horvath et al. |
| 8,486,000 B2 | 7/2013 | Coroneo |
| 8,585,629 B2 | 11/2013 | Grabner et al. |
| 8,663,303 B2 | 3/2014 | Horvath et al. |
| 8,721,702 B2 | 5/2014 | Romoda et al. |
| 8,758,290 B2 | 6/2014 | Horvath et al. |
| 8,765,210 B2 | 7/2014 | Romoda et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,974,511 B2 | 3/2015 | Horvath et al. |
| 9,017,276 B2 | 4/2015 | Horvath et al. |
| 9,095,411 B2 | 8/2015 | Horvath et al. |
| 9,095,413 B2 | 8/2015 | Romoda et al. |
| 2001/0025150 A1 | 9/2001 | De Juan, Jr. et al. |
| 2001/0056254 A1 | 12/2001 | Cragg et al. |
| 2002/0099434 A1 | 7/2002 | Buscemi et al. |
| 2002/0133168 A1 | 9/2002 | Smedley et al. |
| 2002/0177856 A1 | 11/2002 | Richter et al. |
| 2002/0188308 A1 | 12/2002 | Tu et al. |
| 2003/0015203 A1 | 1/2003 | Makower et al. |

(56) References Cited

U.S. PATENT DOCUMENTS

| | | |
|---|---|---|
| 2003/0050574 A1 | 3/2003 | Krueger |
| 2003/0060752 A1 | 3/2003 | Bergheim et al. |
| 2003/0079329 A1 | 5/2003 | Yaron et al. |
| 2003/0093084 A1 | 5/2003 | Nissan et al. |
| 2003/0097053 A1 | 5/2003 | Itoh |
| 2003/0187383 A1 | 10/2003 | Weber et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0050392 A1 | 3/2004 | Tu et al. |
| 2004/0077987 A1 | 4/2004 | Rapacki et al. |
| 2004/0088048 A1 | 5/2004 | Richter et al. |
| 2004/0147870 A1 | 7/2004 | Burns et al. |
| 2004/0210209 A1* | 10/2004 | Yeung ............... A61B 17/7061 604/500 |
| 2004/0215133 A1 | 10/2004 | Weber et al. |
| 2004/0216749 A1 | 11/2004 | Tu |
| 2004/0236343 A1* | 11/2004 | Taylor ............... A61F 9/00781 606/108 |
| 2004/0254521 A1 | 12/2004 | Simon |
| 2004/0260227 A1 | 12/2004 | Lisk, Jr. et al. |
| 2005/0049578 A1 | 3/2005 | Tu et al. |
| 2005/0101967 A1 | 5/2005 | Weber |
| 2005/0125003 A1 | 6/2005 | Pinchuk et al. |
| 2005/0143363 A1 | 6/2005 | De Juan et al. |
| 2005/0246023 A1 | 11/2005 | Yeung |
| 2005/0267398 A1 | 12/2005 | Protopsaltis et al. |
| 2005/0271704 A1 | 12/2005 | Tu et al. |
| 2005/0277864 A1 | 12/2005 | Haffner et al. |
| 2006/0052721 A1 | 3/2006 | Dunker et al. |
| 2006/0064112 A1 | 3/2006 | Perez |
| 2006/0106370 A1 | 5/2006 | Baerveldt et al. |
| 2006/0116625 A1 | 6/2006 | Renati et al. |
| 2006/0149194 A1 | 7/2006 | Conston et al. |
| 2006/0155238 A1 | 7/2006 | Shields |
| 2006/0173397 A1 | 8/2006 | Tu et al. |
| 2006/0173446 A1 | 8/2006 | Dacquay et al. |
| 2006/0200113 A1 | 9/2006 | Haffner et al. |
| 2006/0241411 A1 | 10/2006 | Field et al. |
| 2007/0093783 A1 | 4/2007 | Kugler et al. |
| 2007/0118065 A1 | 5/2007 | Pinchuk et al. |
| 2007/0118066 A1 | 5/2007 | Pinchuk et al. |
| 2007/0123812 A1 | 5/2007 | Pinchuk et al. |
| 2007/0141116 A1 | 6/2007 | Pinchuk et al. |
| 2007/0172903 A1 | 7/2007 | Toner et al. |
| 2007/0191863 A1* | 8/2007 | De Juan et al. ............... 606/108 |
| 2007/0263172 A1 | 11/2007 | Mura |
| 2007/0293872 A1 | 12/2007 | Peyman |
| 2008/0108933 A1 | 5/2008 | Yu et al. |
| 2008/0147001 A1 | 6/2008 | Al-Marashi et al. |
| 2008/0181929 A1 | 7/2008 | Robinson et al. |
| 2008/0249467 A1 | 10/2008 | Burnett et al. |
| 2008/0281277 A1 | 11/2008 | Thyzel |
| 2008/0312661 A1 | 12/2008 | Downer et al. |
| 2009/0036818 A1 | 2/2009 | Grahn et al. |
| 2009/0043321 A1 | 2/2009 | Conston et al. |
| 2009/0264813 A1 | 10/2009 | Chang |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0173866 A1 | 7/2010 | Hee et al. |
| 2010/0191103 A1 | 7/2010 | Stamper et al. |
| 2010/0249691 A1 | 9/2010 | Van Der Mooren et al. |
| 2011/0098627 A1 | 4/2011 | Wilcox |
| 2011/0118745 A1 | 5/2011 | Yu et al. |
| 2011/0230890 A1 | 9/2011 | Thyzel |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123430 A1 | 5/2012 | Horvath et al. |
| 2012/0123434 A1 | 5/2012 | Grabner et al. |
| 2012/0123435 A1 | 5/2012 | Romoda et al. |
| 2012/0123436 A1 | 5/2012 | Reitsamer et al. |
| 2012/0123437 A1 | 5/2012 | Horvath et al. |
| 2012/0123438 A1 | 5/2012 | Horvath et al. |
| 2012/0123439 A1 | 5/2012 | Romoda et al. |
| 2012/0123440 A1 | 5/2012 | Horvath et al. |
| 2012/0165720 A1 | 6/2012 | Horvath et al. |
| 2012/0165721 A1 | 6/2012 | Grabner et al. |
| 2012/0165722 A1 | 6/2012 | Horvath et al. |
| 2012/0165723 A1 | 6/2012 | Horvath et al. |
| 2012/0197175 A1 | 8/2012 | Horvath et al. |
| 2013/0149429 A1 | 6/2013 | Romoda et al. |
| 2013/0150770 A1 | 6/2013 | Horvath et al. |
| 2013/0253406 A1 | 9/2013 | Horvath et al. |
| 2014/0018720 A1 | 1/2014 | Horvath et al. |
| 2014/0180189 A1 | 6/2014 | Horvath et al. |
| 2014/0236065 A1 | 8/2014 | Romoda et al. |
| 2014/0236066 A1 | 8/2014 | Horvath et al. |
| 2014/0236067 A1 | 8/2014 | Horvath et al. |
| 2014/0243730 A1 | 8/2014 | Horvath et al. |
| 2014/0272102 A1 | 9/2014 | Romoda et al. |
| 2014/0287077 A1 | 9/2014 | Romoda et al. |
| 2015/0005689 A1 | 1/2015 | Horvath et al. |
| 2015/0011926 A1 | 1/2015 | Reitsamer et al. |
| 2015/0045714 A1 | 2/2015 | Horvath et al. |
| 2015/0057591 A1 | 2/2015 | Horvath et al. |
| 2015/0133946 A1 | 5/2015 | Horvath et al. |
| 2015/0290035 A1 | 10/2015 | Horvath et al. |
| 2015/0374545 A1 | 12/2015 | Horvath et al. |
| 2016/0135993 A1 | 5/2016 | Horvath et al. |
| 2016/0135994 A1 | 5/2016 | Romoda et al. |
| 2016/0158063 A1 | 6/2016 | Romoda et al. |

FOREIGN PATENT DOCUMENTS

| | | |
|---|---|---|
| WO | WO-93/09738 A1 | 5/1993 |
| WO | WO-93/13916 A1 | 7/1993 |
| WO | WO-94/13234 A1 | 6/1994 |
| WO | WO-94/21205 A1 | 9/1994 |
| WO | WO-94/26167 A1 | 11/1994 |
| WO | WO-95/08310 A1 | 3/1995 |
| WO | WO-95/27453 A1 | 10/1995 |
| WO | WO-97/00649 A1 | 1/1997 |
| WO | WO 98/23237 | 6/1998 |
| WO | WO-00/56255 A1 | 9/2000 |
| WO | WO 02/074052 | 9/2002 |
| WO | WO-2007/087061 A2 | 8/2007 |

OTHER PUBLICATIONS

Written Opinion in PCT application No. PCT/US2007/072547, mailed Dec. 31, 2008, 8 pages.

International Preliminary Report on Patentability in PCT application No. PCT/US2007/072547, mailed Jun. 1, 2009, 9 pages.

U.S. Appl. No. 14/541,070, filed Nov. 13, 2014, entitled "Intraocular Shunt Inserter".

U.S. Appl. No. 14/697,295, filed Apr. 27, 2015, entitled "Shunt Placement Through the Sclera".

\* cited by examiner

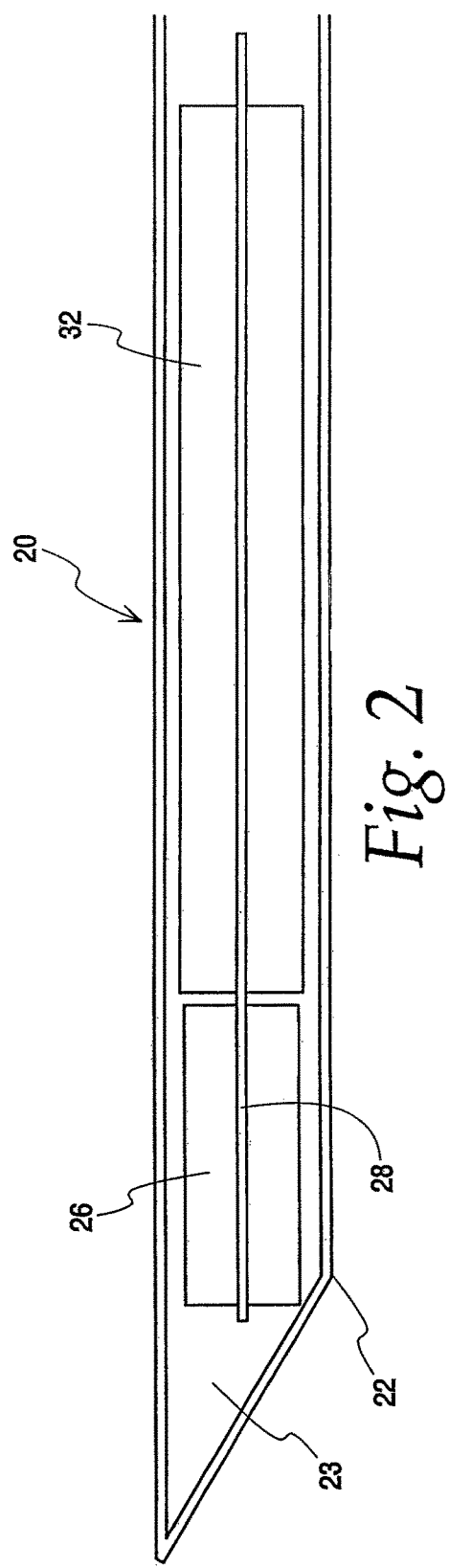
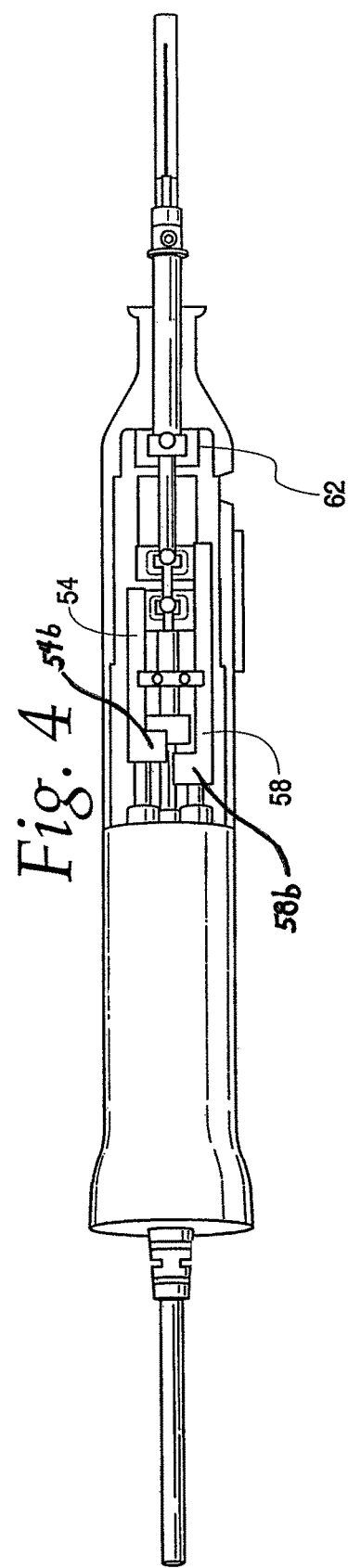

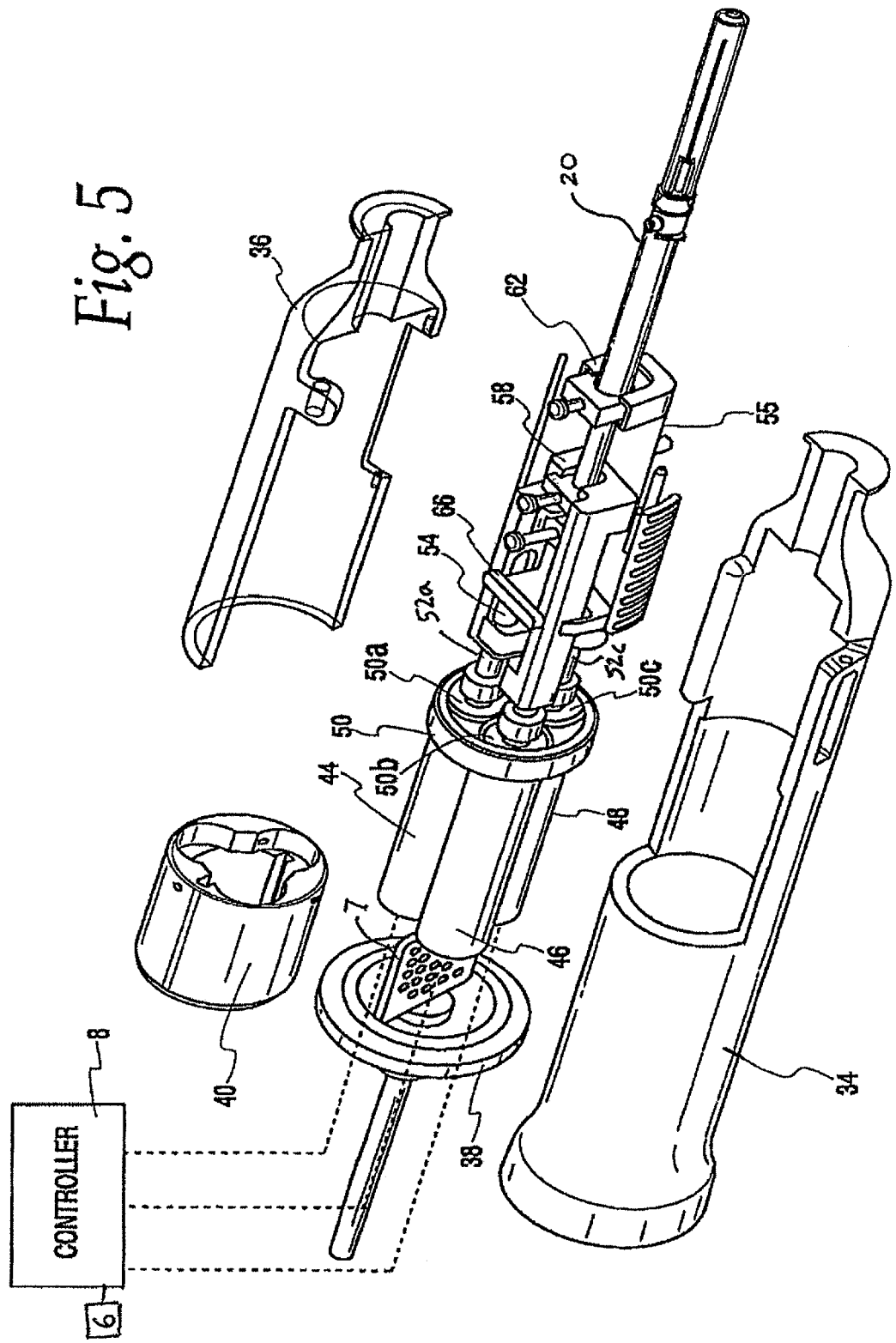

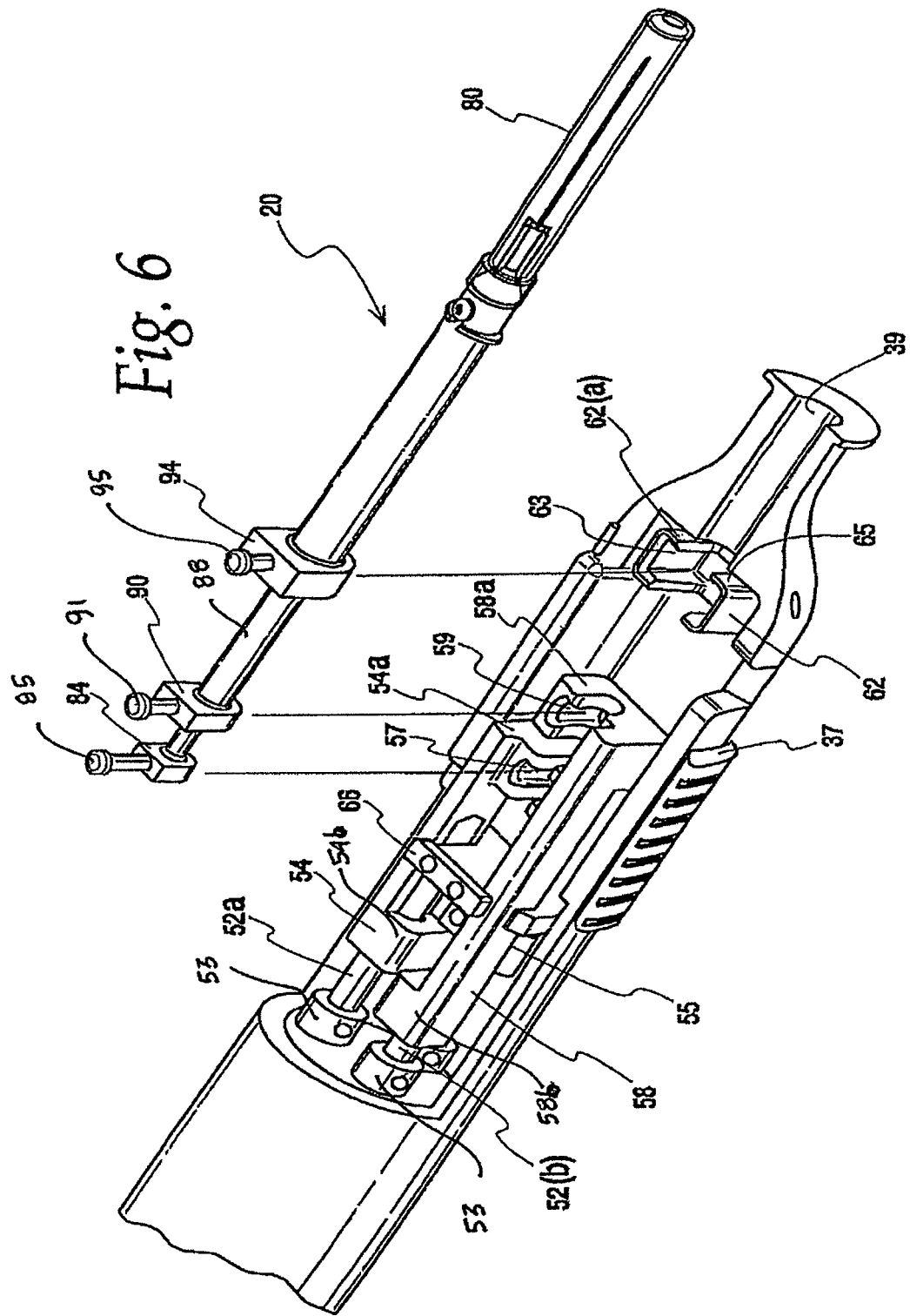

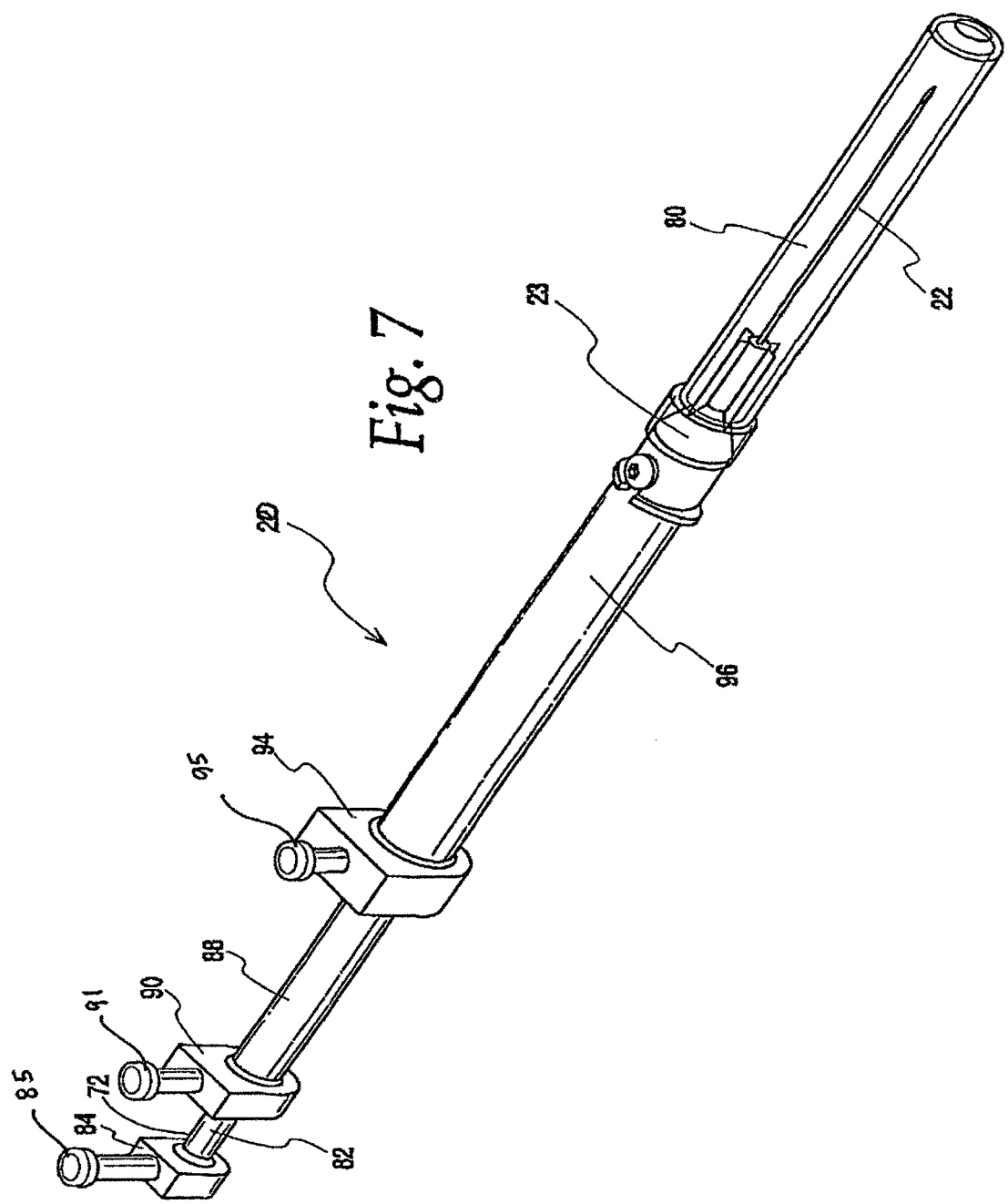

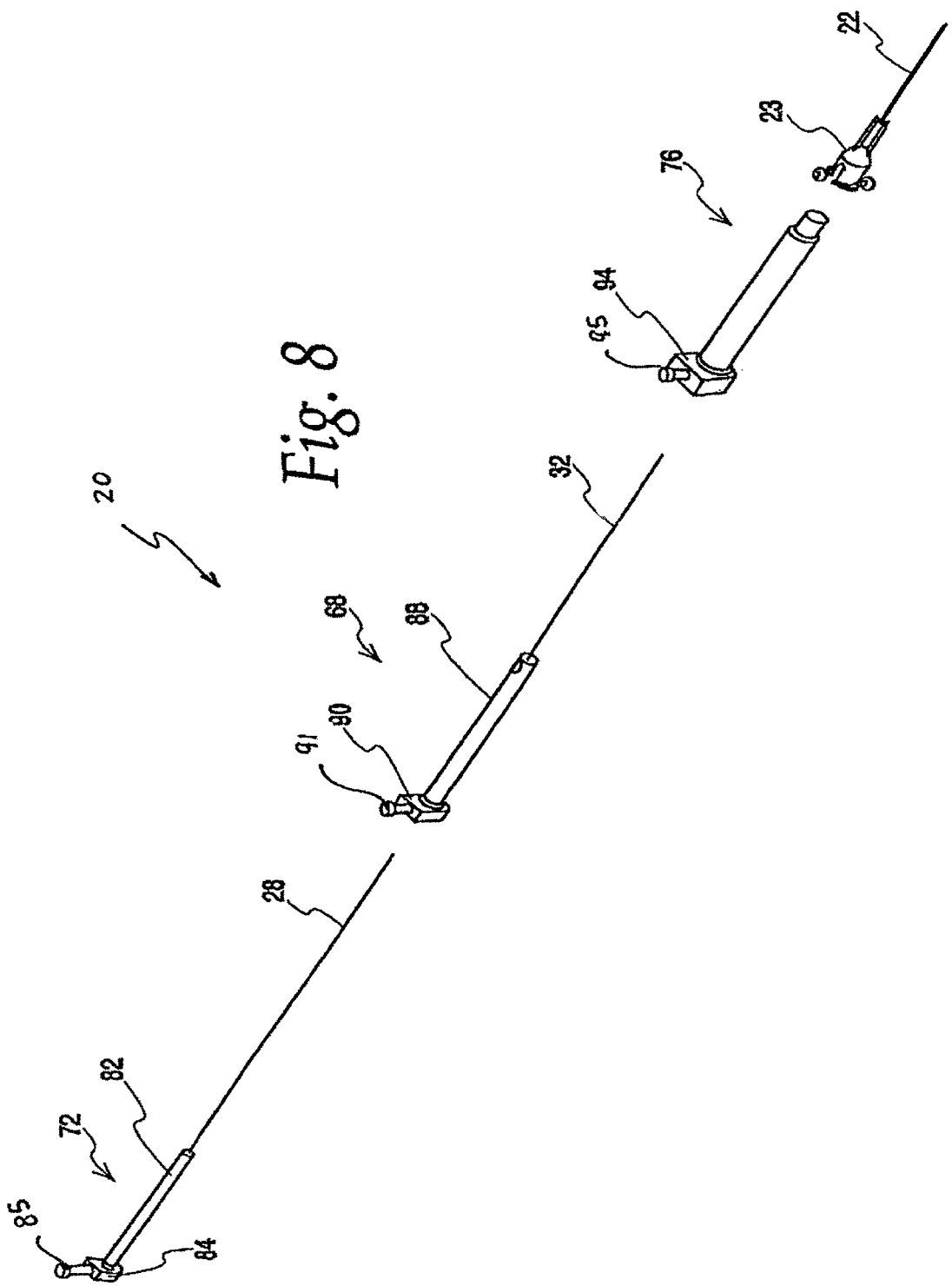

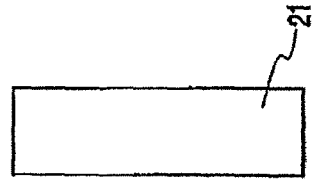
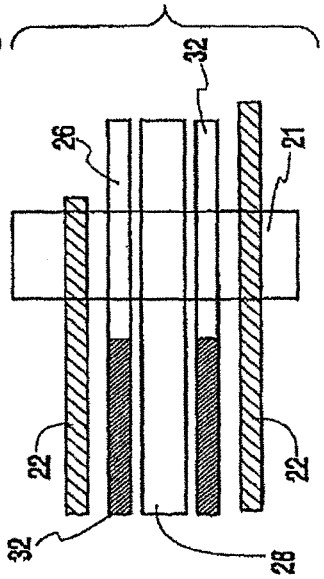
Fig. 9a  Fig. 9b  Fig. 9c
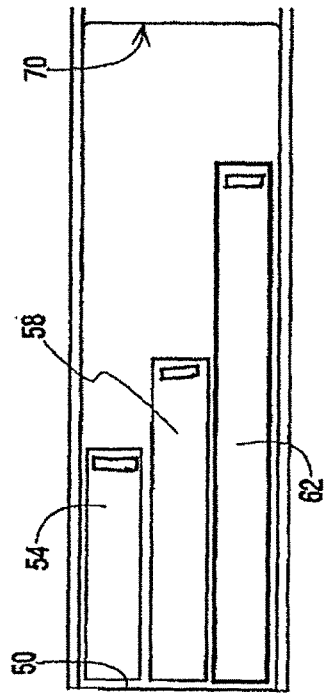
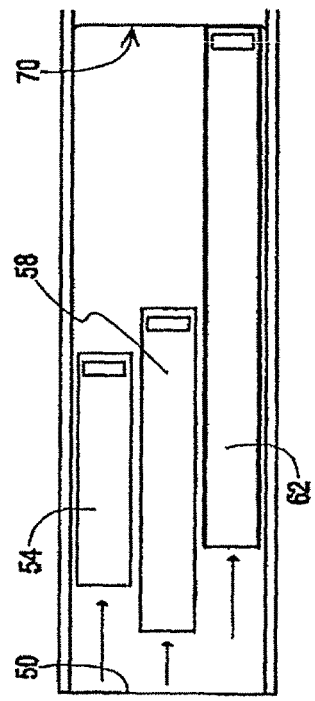
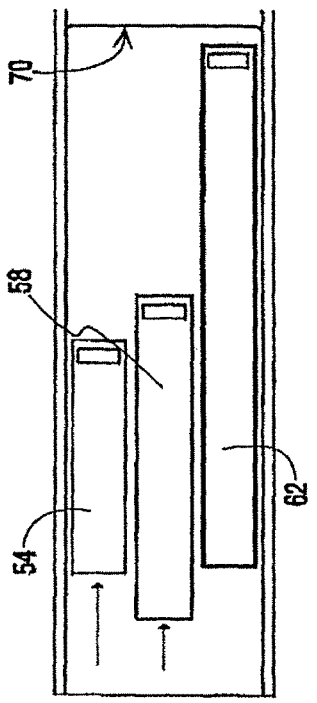

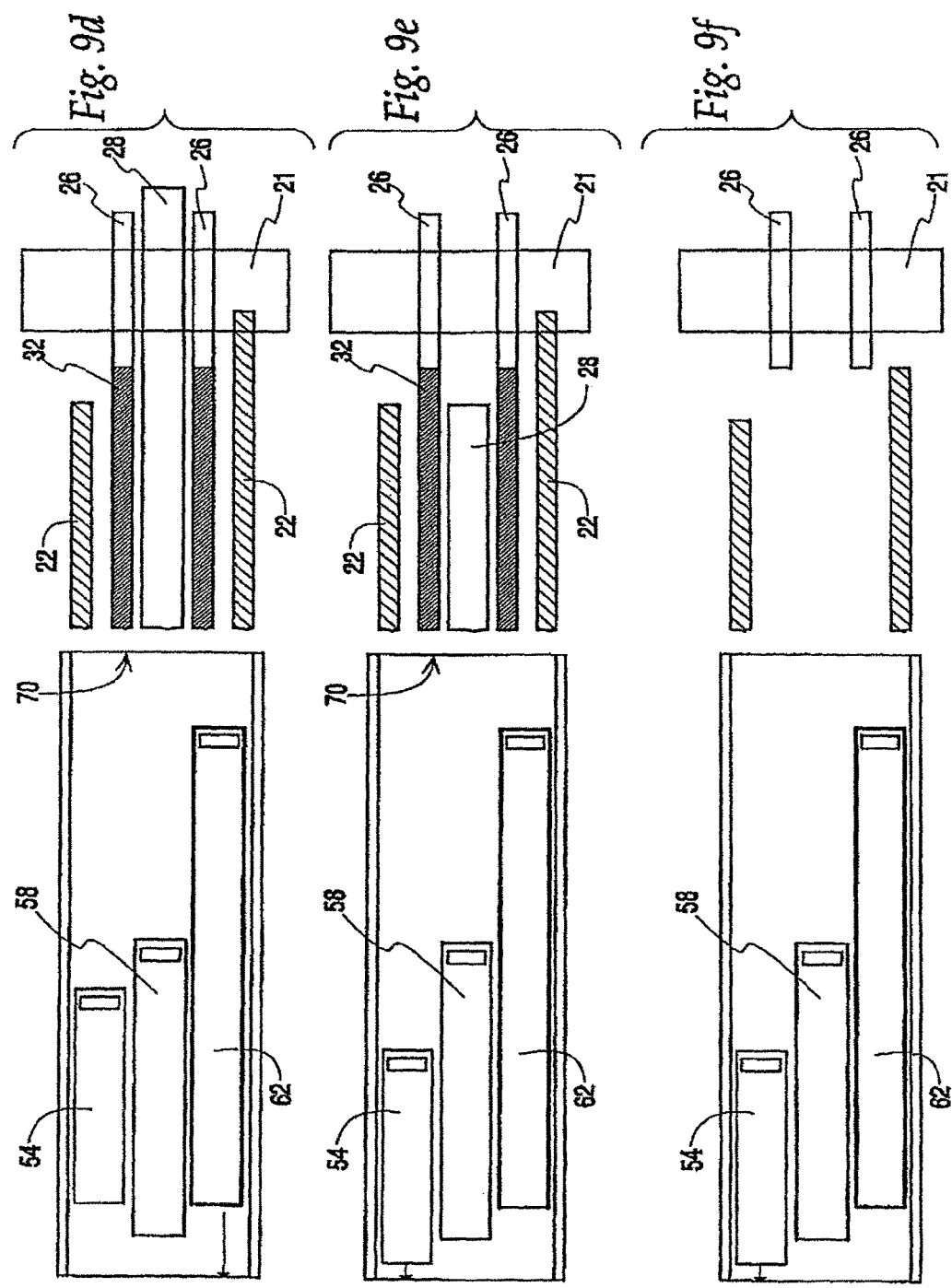

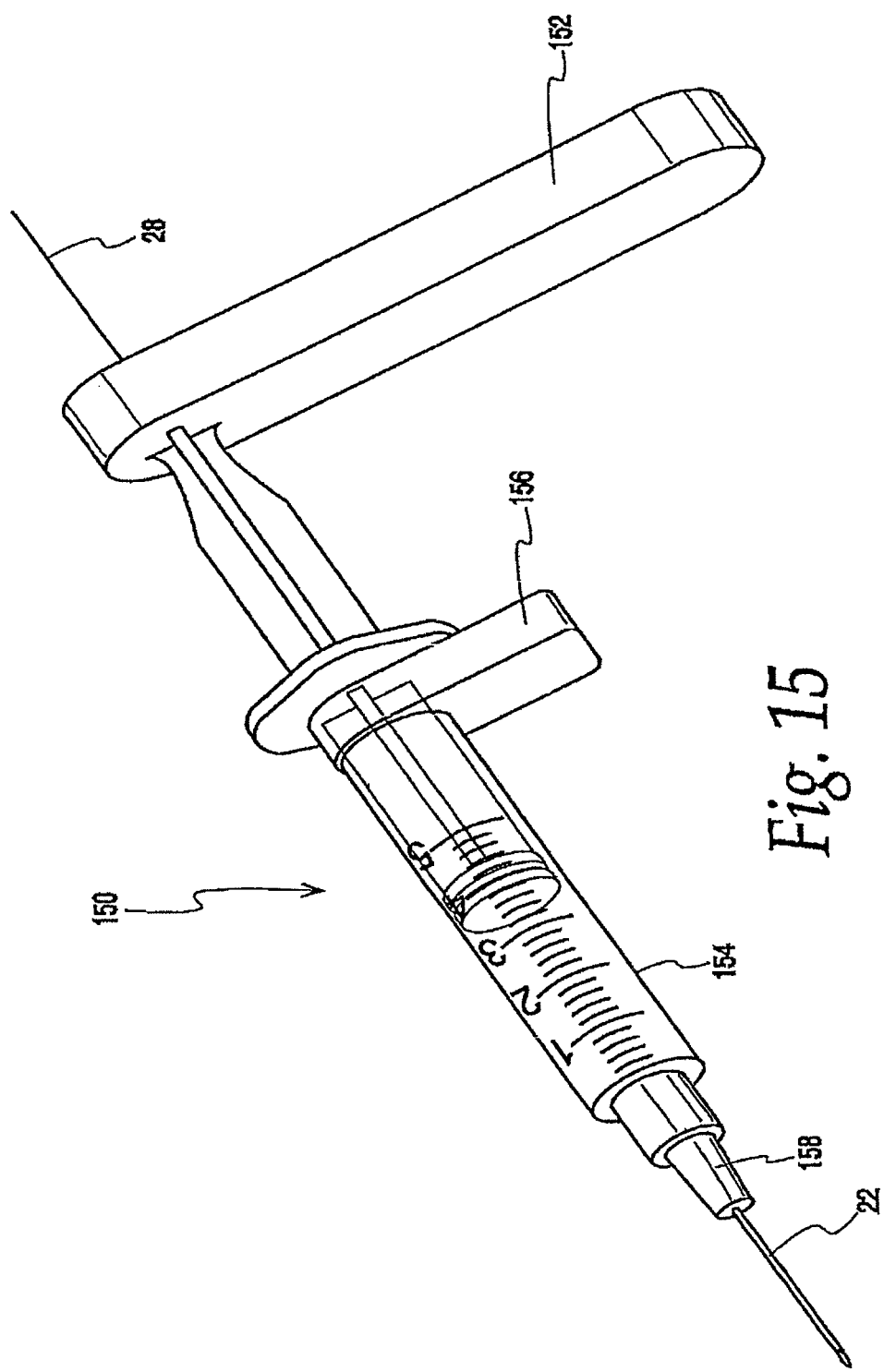

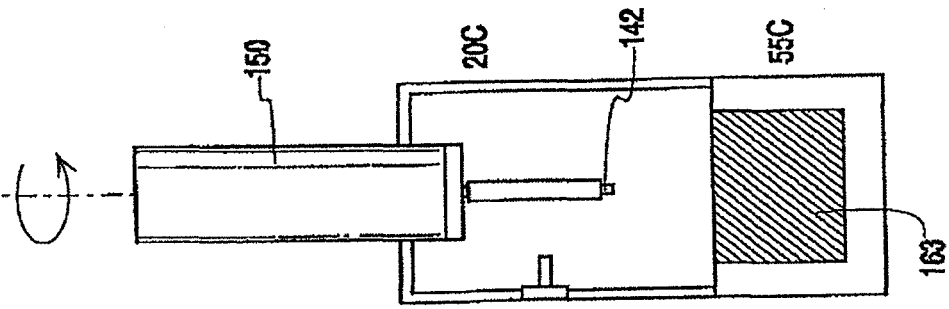
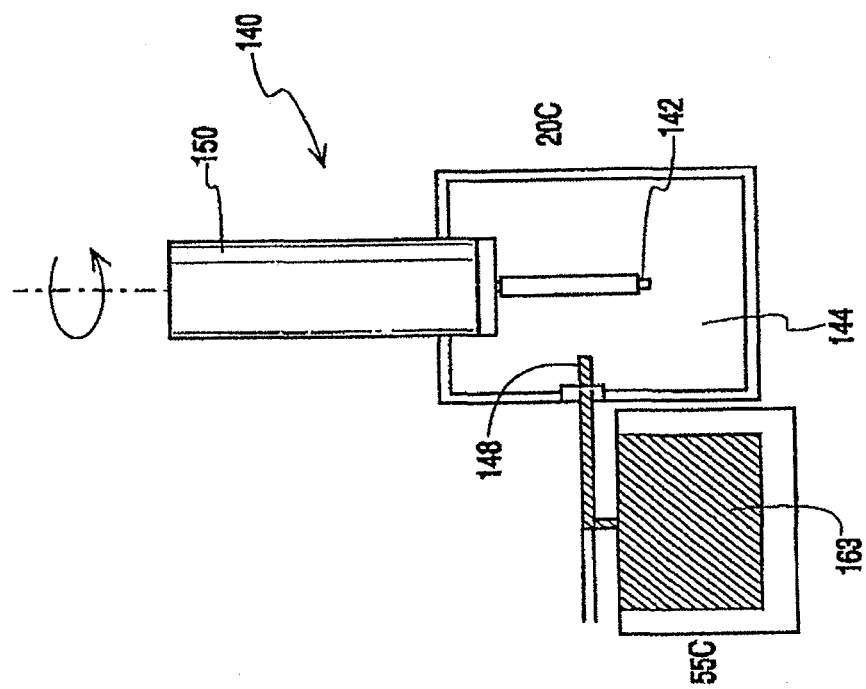

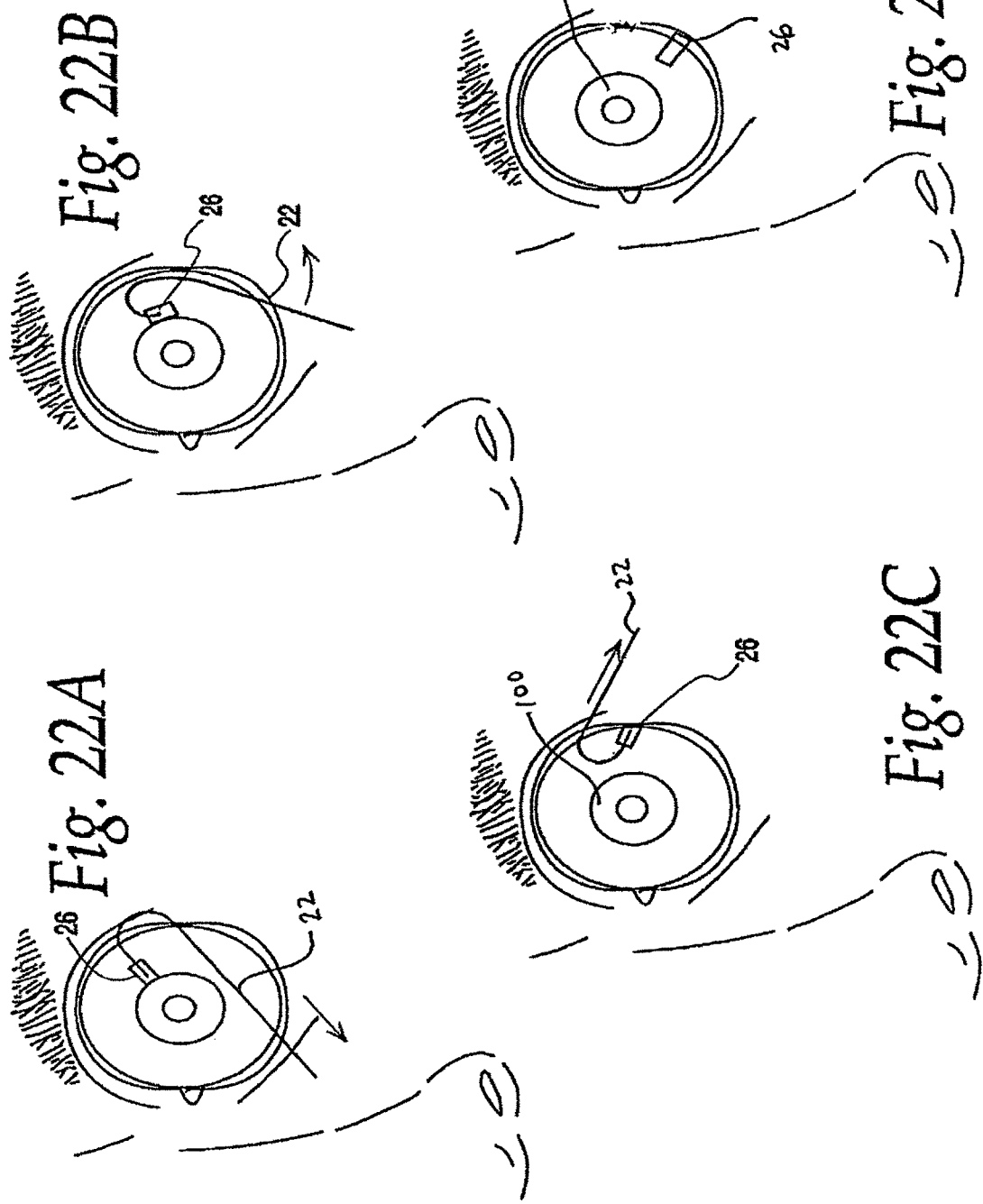

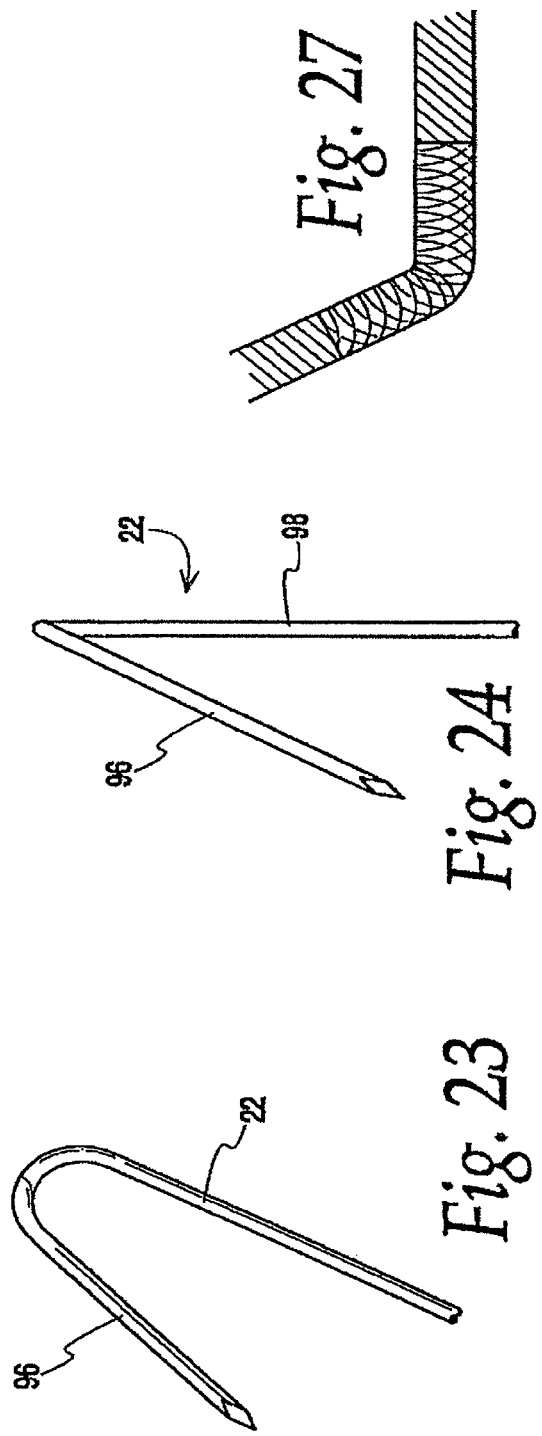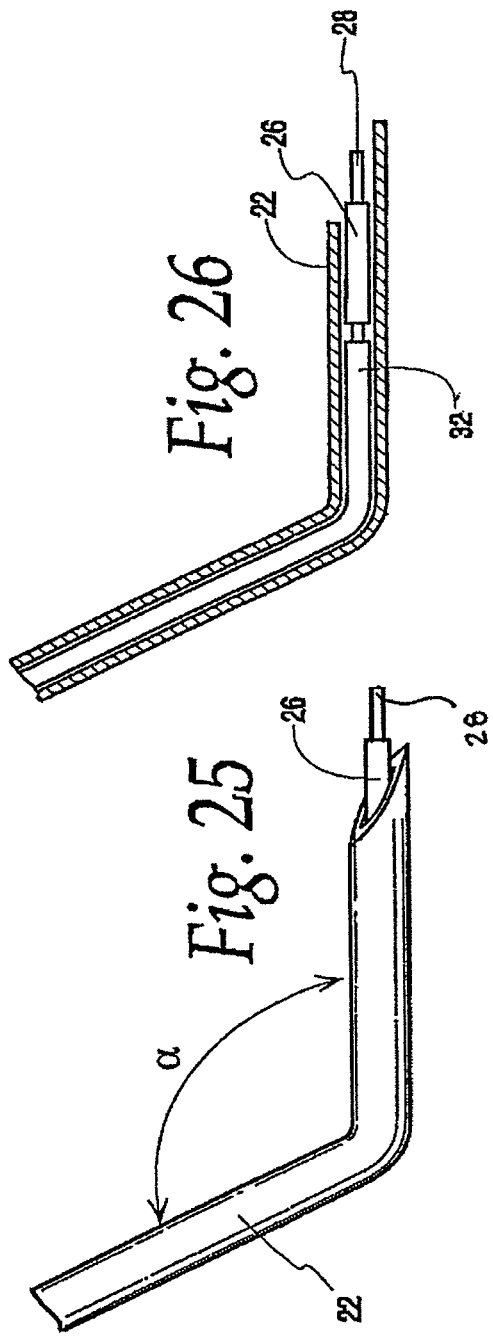

SYSTEMS FOR REDUCING PRESSURE IN AN ORGAN

RELATED APPLICATIONS

This application is a continuation of U.S. application Ser. No. 11/771,805, filed on Jun. 29, 2007, which claims the benefit of and priority to U.S. Provisional Patent Application No. 60/806,402, filed Jun. 30, 2006, both of which are hereby incorporated by reference in their entireties.

BACKGROUND

The present disclosure generally relates to methods, systems and apparatus for relieving fluid pressure from an organ such as (but not limited to) the eye. More particularly, the present disclosure relates to methods and apparatus for treating glaucoma by relieving the pressure within the eye.

Glaucoma is a disease of the eye that affects millions of people. Glaucoma is associated with an increase in intraocular pressure resulting either from a failure of the eye's drainage system to adequately remove aqueous humor from the anterior chamber of the eye or the overproduction of aqueous humor by the ciliary body. The build-up of aqueous humor and resulting intraocular pressure can cause irreversible damage to the optic nerve and the retina, which may potentially lead to irreversible retinal damage and blindness.

Presently, glaucoma can be treated in a number of different ways, The most widely practiced treatment of glaucoma involves delivery of drugs such as beta-blockers or prostaglandins to the eye (typically in the form of eye drops) to either reduce the production of aqueous humor or increase the flow of aqueous humor from the anterior chamber of the eye. Glaucoma may also be treated by surgical intervention such as trabeculectomy. Trabeculectomy or similar surgical procedures involve creating conduits between the anterior chamber and the various structures involved in aqueous humor drainage such as Schlemm's canal, the sclera, and the subconjunctival space in order to provide a pathway for the aqueous humor to exit the anterior chamber.

While these methods of treating glaucoma have been generally effective, they are not without their drawbacks. In the case of medicinal treatments of the eye, patient compliance is an issue because such treatments require regular (i.e., daily) intervention. With respect to surgical procedures such as a trabeculectomy, such procedures are very invasive and can cause irreversible changes to the eye. For example, trabeculectomy results in the permanent removal of a segment of the trabecular meshwork, inflammation and scarring in the quadrant of the eye where the surgery was performed, and the formation of a filtering bleb. Implantation of shunts such as the Molteno, Barveldt, or Ahmed shunts induce chronic foreign body reactions and the formation of a chronic subconjunctival bleb. In addition, such surgical treatment of glaucoma often requires long healing times and can result in certain complications such as infection, scarring, hypotony or cataracts.

More recently, less invasive surgical treatments have been developed. These treatments do not require incision into the conjunctiva of the eye. One example of a less invasive surgical procedure is described in U.S. Pat. No. 6,544,249, the entire disclosure of which is hereby incorporated by reference. U.S. Pat. No. 6,544,249 discloses methods and apparatus for introducing a small bioabsorbable and biocompatible drainage canal, referred to therein as a microfistula tube into the portion of the eye that extends from the anterior chamber to the sub-conjunctival space. The procedure described in U.S. Pat. No. 6,544,249 does not require incision of the conjunctiva. Instead, introduction of the bioabsorbable microfistula tube is accomplished by an ab interno approach—through the cornea of the eye to the desired location (between the anterior chamber and the sub-conjunctival space.) U.S. Pat. No. 6,544,249 also generally describes a delivery apparatus for introducing and implanting the bioabsorbable microfistula tube.

U.S. Pat. No. 6,007,511, the entire disclosure of which is incorporated herein by reference, likewise discloses less invasive methods and apparatus for treating glaucoma. As in the above-referenced U.S. Pat. No. 6,544,249, a bioabsorbable drainage tube is introduced into the area between the anterior chamber and the sub-conjunctival space to allow drainage of the aqueous humor from the anterior chamber of the eye. As in U.S. Pat. No. 6,544,249, incision of the conjunctiva is not required.

These new procedures for treating glaucoma offer the promise of a long term cure of glaucoma without the shortcomings of medicinal treatments and without the risks associated with the known and presently practiced surgical procedures described above. Accordingly, it would be desirable to provide improved methods, systems, channels and delivery apparatus for treating glaucoma specifically and for treating other conditions where drainage of accumulated liquid is desired or required.

SUMMARY OF THE INVENTION

The present disclosure sets forth improved methods and apparatus for carrying out channel implantation into an organ of the body such as the eye. It will be appreciated that the methods and apparatus described below may also find application in any treatment of a body organ requiring controlled drainage of a fluid from the organ. Nonetheless, the methods and apparatus for performing such treatment will be described relative to the eye and, more particularly, in the context of treating glaucoma.

The present disclosure relates to an implantable, microfistula channel. The channel has a bioabsorbable body defining an interior flow path. The channel body is made of cross-linked bioabsorbable material such as gelatin and has an expandable outer diameter. The flow path has a diameter of between approximately 50 and 250 microns ($\mu$m).

The present disclosure also relates to a method of making an implantable channel. The method includes providing a source of a bio-compatible gelatin solution and providing a generally cylindrical solid support. The support has a diameter of approximately 50 to 250 microns. The method includes contacting the outer surface of the support with the gelatin for a period of time sufficient to coat the support outer surface. A hollow gelatin tube is thus formed on the support. The formed hollow gelatin channel may be dried (cured) for a selected period of time and the formed gelatin tube may be subjected to a cross-linking treatment. The formed and cross-linked gelatin tube is removed from the support.

The present disclosure also relates to an implantation apparatus for implanting a channel into an organ of a subject. The apparatus includes a reusable portion that includes an apparatus housing. The housing has an open distal end, a proximal end and an interior chamber. The apparatus includes an arm subassembly within the housing that includes one or more movable arms adapted to engage a disposable needle assembly. The apparatus further includes one or more drivers coupled to said one or more moveable arms of the arm sub-assembly.

The present disclosure further relates to systems for implanting a channel into an organ of a subject. The system includes a reusable portion adapted to receive a needle assembly and a disposable portion that includes a needle assembly. The needle assembly has a hollow needle terminating in a sharpened tip and a guidewire and a plunger disposed within the needle. The system includes a microprocessor-based controller including pre-programmed instructions for selective movement of at least the guidewire and the plunger.

The present disclosure further relates to methods of implanting a bioabsorbable channel into an organ of a subject. In the methods described herein, an implantation apparatus including a hollow needle having a pointed distal end, a bioabsorbable channel within the needle assembly and a plunger proximally located relative to the channel is provided. The method includes the steps of introducing the pointed tip of the needle end assembly into the organ of a subject, advancing the needle to the desired area of implantation and actuating the plunger to advance the channel to the desired area of implantation. The method further includes removing the needle from the organ.

BRIEF DESCRIPTION OF THE DRAWINGS

FIG. 2 is an enlarged, schematic view of the distal end of one embodiment of an implantation apparatus described herein;

FIG. 4 is a top view of the apparatus of FIG. 3 with front door removed;

FIG. 5 is an exploded view of the system for implanting a channel including the apparatus FIG. 3;

FIG. 6 is a perspective view of the distal end of the apparatus of FIG. 3 with the needle assembly separated therefrom;

FIG. 7 is an enlarged perspective view of the needle assembly of FIG. 6;

FIG. 8 is an exploded view of the needle assembly of FIG. 7;

FIG. 9(a)-(f) are schematic views of the implantation apparatus of FIG. 3 showing the plunger, guidewire and needle arms in different positions during the positioning and/or implantation steps as they correspond to the positions of the plunger, guidewire, needle and channel within the eye;

FIG. 15 is a perspective view of a syringe type, manually operated, handheld implantation apparatus;

FIG. 16 is a schematic illustration of a method and apparatus for making a gelatin microfistula channel in the form of a tube;

FIG. 17 is a schematic illustration an alternative embodiment of an apparatus for making a gelatin microfistula tube;

FIG. 22(a)-(d) depicts a series of steps showing an ipsilateral normal channel insertion and placement using a U-shaped or otherwise arcuate needle;

FIG. 23 is a perspective view of a U-shaped needle of the type shown in the method of insertion and placement shown in FIGS. 22(a)-(d);

FIG. 24 is a front view of the U-shaped needle of FIG. 23;

FIG. 25 is a side view of a needle having a bend at its distal end portion including the guidewire and channel inserted therein;

FIG. 26 is a cross-sectional view of the needle, guidewire, plunger and channel of the needle distal end portion of FIG. 25;

FIG. 27 is a side view of the needle, the plunger or guidewire of FIG. 25, wherein a portion of the plunger or guidewire facilitates bending of the same;

DETAILED DESCRIPTION OF THE INVENTION

Figure 1:
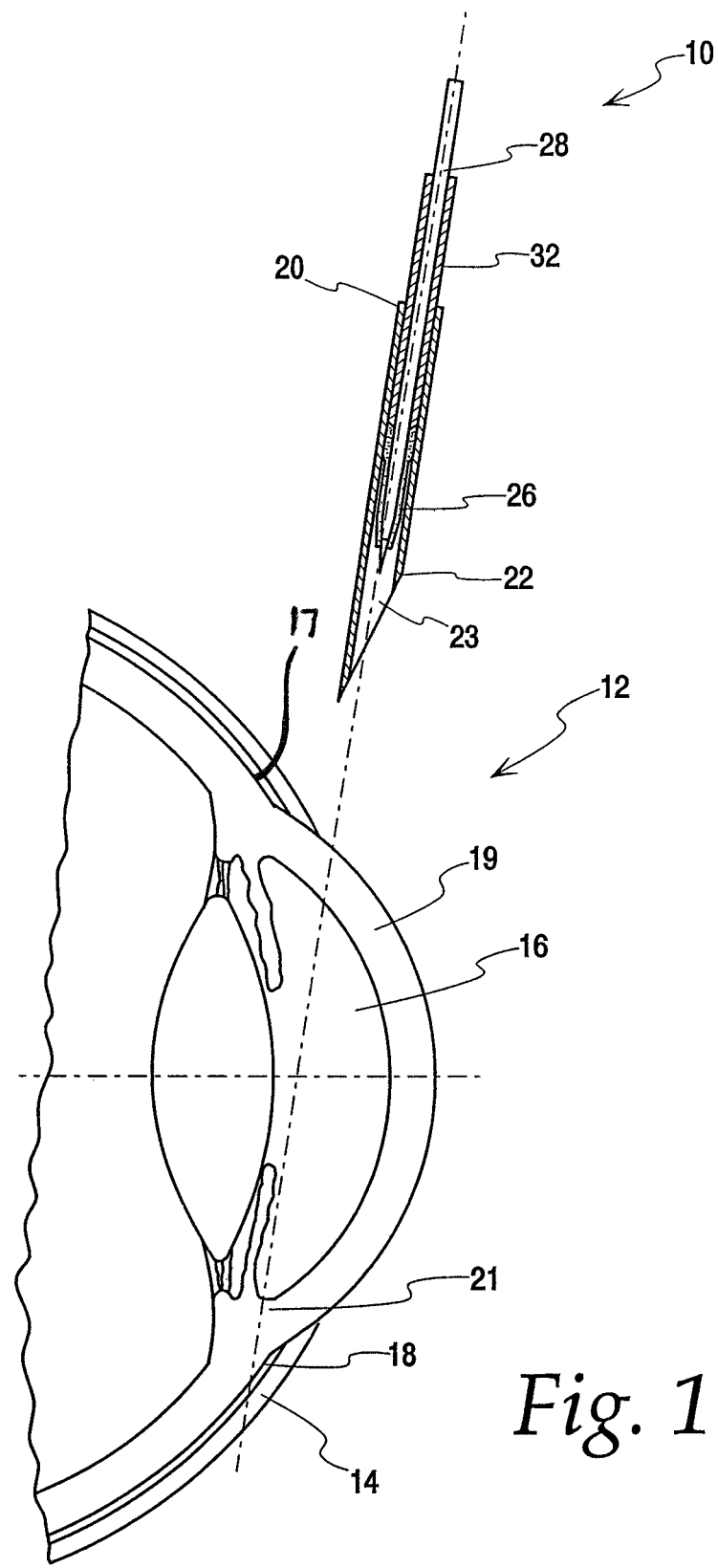
FIG. 1, depicts, in general, a method for implanting a channel, showing in cross section, the distal end of an implantation apparatus.

Methods and apparatus for delivering and implanting bioabsorbable tubes or shunts are generally disclosed in U.S. Pat. Nos. 6,544,249 and 6,007,511, both of which have been previously incorporated by reference in their entireties. As set forth therein, and also with reference to FIG. 1, an implantation apparatus 10 is used to deliver and implant a small micro-sized bioabsorbable tube i.e., the microfistula tube 26, to an area between the anterior chamber 16 and the sub-conjunctival space 18 of the eye 12. The implanted microfistula tube 26 provides a channel that continuously drains aqueous humor from anterior chamber 16 at a desired rate. Microfistula tube 26 remains implanted in the eye, and eventually dissolves.

FIG. 1 illustrates the distal (i.e., "working end") end of the apparatus 10 (including the microfistula tube 26) as it approaches the eye 12 as described in U.S. Pat. No. 6,544,249. Unlike current trabeculectomy procedures, in accordance with the method shown in FIG. 1, needle 22 housing microfistula tube 26 approaches and enters the eye through cornea 19 (ab interno) and not through the conjunctiva 14 (ab externo). This prevents damage to the conjunctiva, improves healing time and reduces the risk of complications that may result from other surgical techniques of the prior art (e.g., trabeculectomy). As further shown and described in U.S. Pat. No. 6,544,249 and in FIG. 1, hollow needle 20 is introduced through the cornea 19 and is advanced across the anterior chamber 16 (as depicted by the broken line) in what is sometimes referred to as a transpupil implant insertion. Channel 26 is eventually implanted in the area spanning the sclera 21, anterior chamber 16 and the sub-conjunctival space 18 (see also FIG. 8 of U.S. Pat. No. 6,544,249).

The methods, systems, apparatus and channels described herein likewise utilize a hollow needle and a bioabsorbable channel delivered by the needle ab interno through the cornea 19 or the surgical limbus 17. As used herein, the term "channel" includes hollow microfistula tubes similar to the type generally described in U.S. Pat. No. 6,544,249 as well as other structures that include one or more flow paths therethrough.

Turning now to a discussion of the methods, systems, apparatus and channels that embody the present invention, as generally shown in FIG. 2, the working end of implantation apparatus is provided as a needle assembly 20 that includes a hollow needle 22 defining an inner chamber 23 and terminating in a sharpened tip. Placed within inner chamber 23 of the hollow needle 22 is a cylindrical inner tube or plunger 32 that is coaxial with needle 22. In the loaded and ready to use condition, channel 26 is also placed or otherwise disposed within the hollow chamber 23 of needle 22 and is distally located relative to plunger 32. Both channel 26 and plunger 32 may be placed over and supported by optional guidewire 28. As described in U.S. Pat. No. 6,544,249 and in this disclosure, through relative movement of needle 22, plunger 32, guidewire 28, and channel 26 can be implanted into eye 12. As noted above, guidewire 28 is optional and may be omitted where placement and advancement of channel 26 does not require one.

As will be described in greater detail below, channel 26 may be delivered to and implanted within the desired location of the eye in any one of several different ways. The method of implantation (and system) may be fully automated, partially automated (and, thus, partially manual) or completely manual. For example, in a fully automated procedure, channel 26 may be delivered by robotic implantation whereby a surgeon controls the advancement of needle 22, plunger 32, optional guidewire 28 and, as a result, channel 26 by remotely controlling a robot. In such fully automated, remotely controlled procedures, the surgeon's hands typically do not contact implantation apparatus 10 during the surgical procedure.

Alternatively, channel 26 may be delivered to the desired area of the eye with a "handheld" implantation apparatus, embodiments of which are shown in FIGS. 2-15 and described below. In one example of a handheld implantation apparatus, discussed in more detail below, movement of the channel 26, needle 22, and plunger 32 and optional guidewire 28 may be controlled remotely by an operator using a microprocessor-based device i.e., "controller," while implantation apparatus 10 is physically held by the surgeon. Insertion of the needle into the eye as well as certain repositioning or adjusting steps may be performed manually by the surgeon.

In the case of fully manual apparatus and methods, which are also discussed below and shown in FIGS. 12-15, all of the positioning, repositioning, adjusting and implantation steps are performed manually by the surgeon.

One example of an implantation apparatus 10 and system embodying the present invention is shown in FIGS. 3-9. Although apparatus 10 shown in FIGS. 3-9 is preferably a handheld type implantation apparatus where relative movement of the needle, optional guidewire and plunger is accomplished automatically by pre-programmed instructions in a microprocessor-based controller and at least some of the steps may be manually performed by the surgeon, apparatus 10 can also be used in a fully automated environment. In any event, implantation apparatus 10 shown in FIG. 3 includes a reusable portion 30 and a disposable portion embodied in needle assembly 20. As will be discussed in greater detail below, needle assembly 20 is separately provided and is received by arm sub-assembly 55 of implantation apparatus 30.

Figure 3:
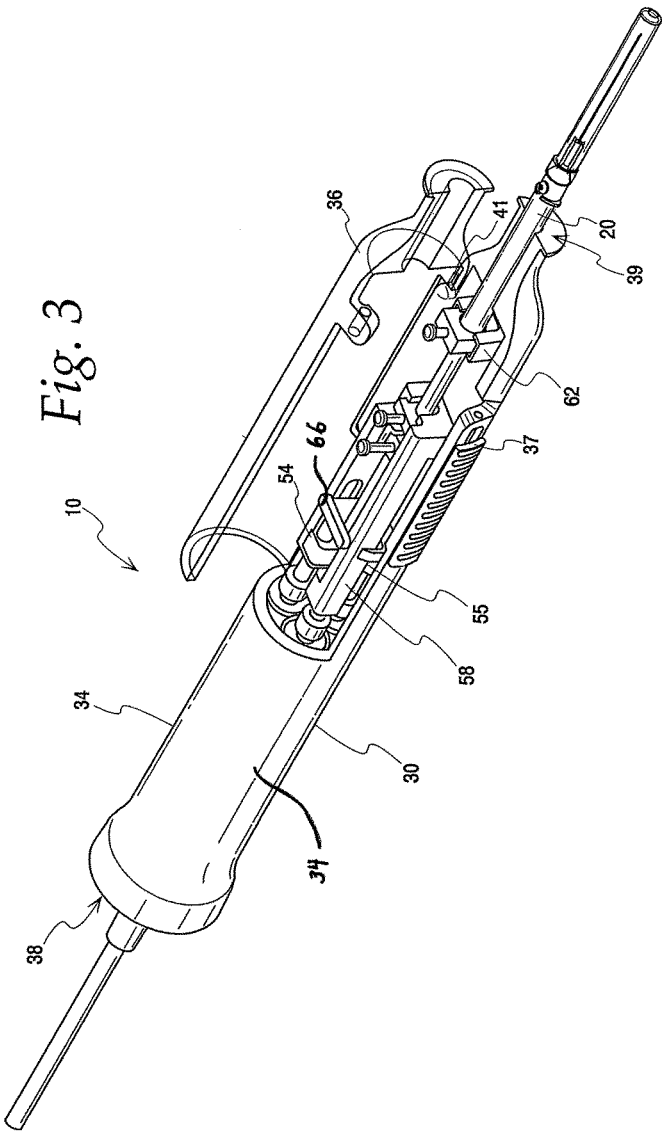
FIG. 3 is a perspective view of one embodiment of a handheld implantation apparatus with the door opened and a needle assembly installed therein.

As shown in FIG. 3, implantation apparatus 10 includes a generally cylindrical body or housing 34, although as will be appreciated from other embodiments disclosed herein, the body shape of housing 34 is not critical. However, if apparatus 10 is to be held by the surgeon (i.e., a handheld apparatus) the shape of housing 34 should be such that is ergonomical, allowing for comfortable grasping by the surgeon. Housing 34 is closed at its proximal end by end cap 38 and has an opening 39 at its distal end through which at least a portion of needle assembly 20 extends. Door 36 provides access to the interior of housing 34 allowing for easy insertion and removal of needle assembly 20. Locking means such as slide lock 37 may be provided to secure door 36 to (and release door 36 from) housing 34. Door 36 may be secured to housing 34 by a hinge 41 allowing the door to swing open when it is unlocked. In an alternative embodiment, door 36 may be slidably attached to housing 34 and access to the interior of housing 34 may be achieved by sliding door 36 toward the proximal end of the housing 34. Of course, it will be appreciated that other ways of providing access to the interior of the implantation apparatus 10 are also possible.

Housing 34 and door 36 may be made of any material that is suitable for use in medical devices. For example, housing 34 may be made of a lightweight aluminum or, more preferably, a biocompatible plastic material. Examples of such suitable plastic materials include polycarbonate and other polymeric resins such as Delrin® and Ultem®. Similarly, door 36 may be made of a plastic material such as the above-described materials including polymers and polymer resins such as polycarbonate, Delrin® and Ultem®. In a preferred embodiment, door may be substantially translucent or transparent.

Re-usable portion 30 of implantation apparatus 10 houses the components required to effect movement of the needle assembly 20 components during the implantation procedure. As shown in FIGS. 3-6, implantation apparatus 10 houses a plurality of moveable arms, collectively referred to herein as the arm sub-assembly 55, which is adapted to receive needle assembly 20. Arms 54, 58 and 62 are axially moveable between the proximal and distal ends of apparatus 10 and are coupled to lead screws 52(a)-(c) at their distal ends which, in turn, are coupled to one or more drivers 44, 46, 48. In the embodiment shown in FIGS. 3-6, drivers are preferably a plurality of gear or stepper motors 44, 46 and 48. Alternatively, arms may be driven pneumatically or otherwise.

With respect to the embodiments of FIGS. 3-6, motors 44, 46 and 48 are housed near the proximal end of implantation apparatus 10. Motors 44, 46 and 48 may be stacked or bundled in parallel in the manner shown in FIG. 5 and held in place by front motor mount 50 and rear motor mount 40.

As indicated above, each of the motors 44, 46 and 48 (or other drivers) is coupled to one of the lead screws 52(a)-(c), which, in turn, are coupled to movable arms 54, 58 and 62 of arm sub-assembly 55. For example, with specific reference to the embodiment of FIGS. 3-6, lead screw 50(a) is coupled to guidewire arm 54; lead screw 50(b) is coupled to plunger arm 58; and lead screw 50(c) is coupled to needle arm 62. Motors 44, 46 and 48 may be selectively and independently activated by switches on the apparatus 10 itself or as schematically shown in FIG. 5 as described, may be coupled to a remote controller 8 of the system. In one embodiment, apparatus 10 includes printed circuit board 7 which establishes an electrical connection between motors 44, 46 and 48 and controller 8. Controller 8 may include a control box that supplies power and pre-programmed positioning instructions to the implantation apparatus 30 generally and motors 44, 46 and 48, specifically. Movements of the various arms 54, 58 and 62 can be initiated by the surgeon via a foot switch or other type of remote control 6.

As shown in the Figures, arms 54, 58 and 62 are preferably of varying axial lengths. Each of the arms 54, 58 and 62 includes a slot for receiving a portion of the needle assembly 20 (described below.) Thus, guidewire arm 54 includes a guidewire hub slot 57; plunger arm 58 includes a plunger hub slot 59 and needle arm 62 includes a needle hub slot 63.

In a preferred embodiment, each of the arms 54, 58 and 62 includes at its distal and/or proximal ends a portion having an enlarged cross-section. The distal "blocks" 54(a), 58(a) and 62(a) provide abutment surfaces which limit axial movement of the respective arms. As will be seen from the discussion of the implantation method, the distal blocks which also define slots 59, 62 and 63 limit movement of the particular arms, thereby ensuring that the guidewire, plunger and channel 26 do not move beyond a pre-determined distance. Similarly, wall 65 of housing 34 limits movement of needle arm 62, likewise ensuring that the needle does not penetrate the eye beyond a desired distance. Proximal blocks 58(a), 58(b) and 58(c) (not shown) likewise provide an abutment surfaces for contacting fixed collars 53 on lead screws 52(a)-(c). Contact between the surfaces of blocks 58(a), 58(b) and 58(c) and respective collars 53 provides an indication that arms of arm subassembly 55 are in their rearmost or "hard stop" position, discussed below. Blocks 58(a)-(c) also include internal threaded nuts through which lead screws 50(a)-(c) travel.

As further seen in FIGS. 3-6, implantation apparatus 10 includes a guide block 66 attached to needle arm 62. Guide block 66 defines two partially enclosed apertures for slidably retaining guidewire arm 54 and plunger arm 58. Guide block 66 prevents rotation or other undesired dislocation of guidewire arm 54 and plunger arm 58 and maintains these components in an axially aligned orientation. Guide block 66 also serves as a stop that limits movement of arms 54 and 58.

As noted above, arm sub-assembly 55 is adapted to receive needle assembly 20. Needle assembly, shown in FIGS. 7 and 8 is itself made of a plurality of separate, and co-axially assembled parts. Co-axial assembly of these constituent parts allows for relative axial movement of optional guidewire 28, needle 20 and plunger 32. As shown in FIGS. 7 and 8, in one embodiment, needle assembly includes a guidewire hub 72. In the embodiment shown, guidewire hub 72 includes a distal cylinder 82 and a proximal block 84. Guidewire 28 extends from the cylinder 82 and is received within plunger hub 68 which likewise includes a distal hollow cylinder and proximal block 90. Plunger tube 32 extends from plunger cylinder 88 and when brought together with guidewire hub 72 surrounds guidewire 86 along most of its length. Both guidewire 28 and plunger tube 92 are then received by needle hub 96. A hollow needle 22 attached to needle mount 23 is mounted on needle hub 96. Hollow needle 22 has an inner diameter sufficient to receive the assembled co-axial guidewire 86 and plunger 92. Of course, it will be appreciated that in certain embodiments, a guidewire may not be required and that needle assembly 20 may include a plunger and needle only.

As best shown in FIG. 6, needle assembly 20 is adapted for placement within arm assembly 55. More specifically, guidewire block 84, plunger block 90 and needle block 94 of needle assembly 20 are received by the slots 57, 59 and 63, respectively, of arm sub-assembly 55. Each of blocks 84, 90 and 94 may include an upstanding pin 85, 91 and 95 (respectively). Pins 85, 91 and 95 are of a height sufficient so as to almost contact the inner surface of door 36 (when closed). Providing pins of sufficient height keeps needle assembly from becoming dislodged from sub-assembly 55 in the event that apparatus 10 is rotated by the surgeon. As shown in FIGS. 7 and 8, hollow needle 22 is preferably protected prior to use by removable needle cap 80.

Figure 10:
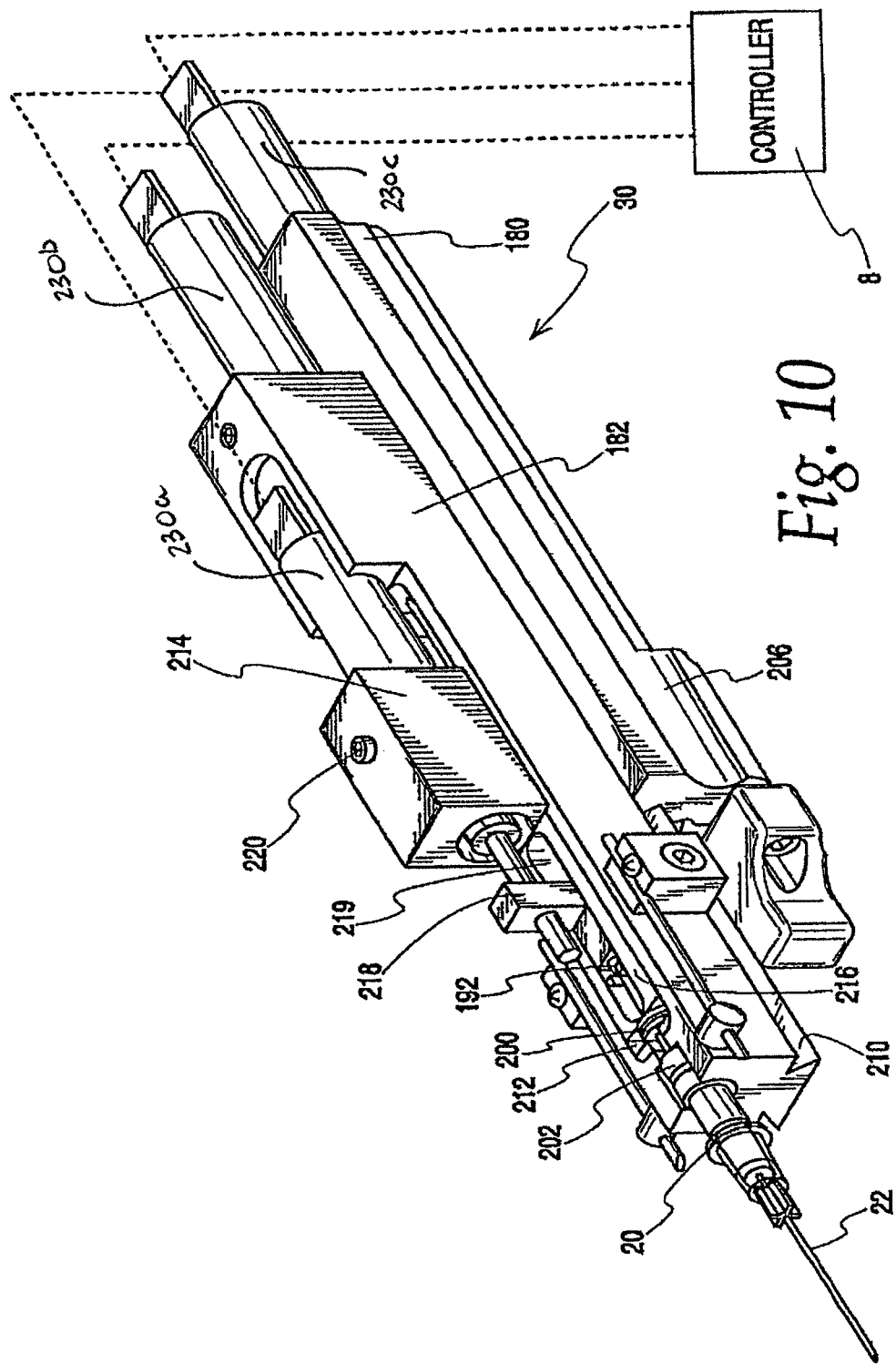
FIG. 10 is a perspective view of another embodiment of an implantation apparatus with the needle assembly installed therein.
Figure 11:
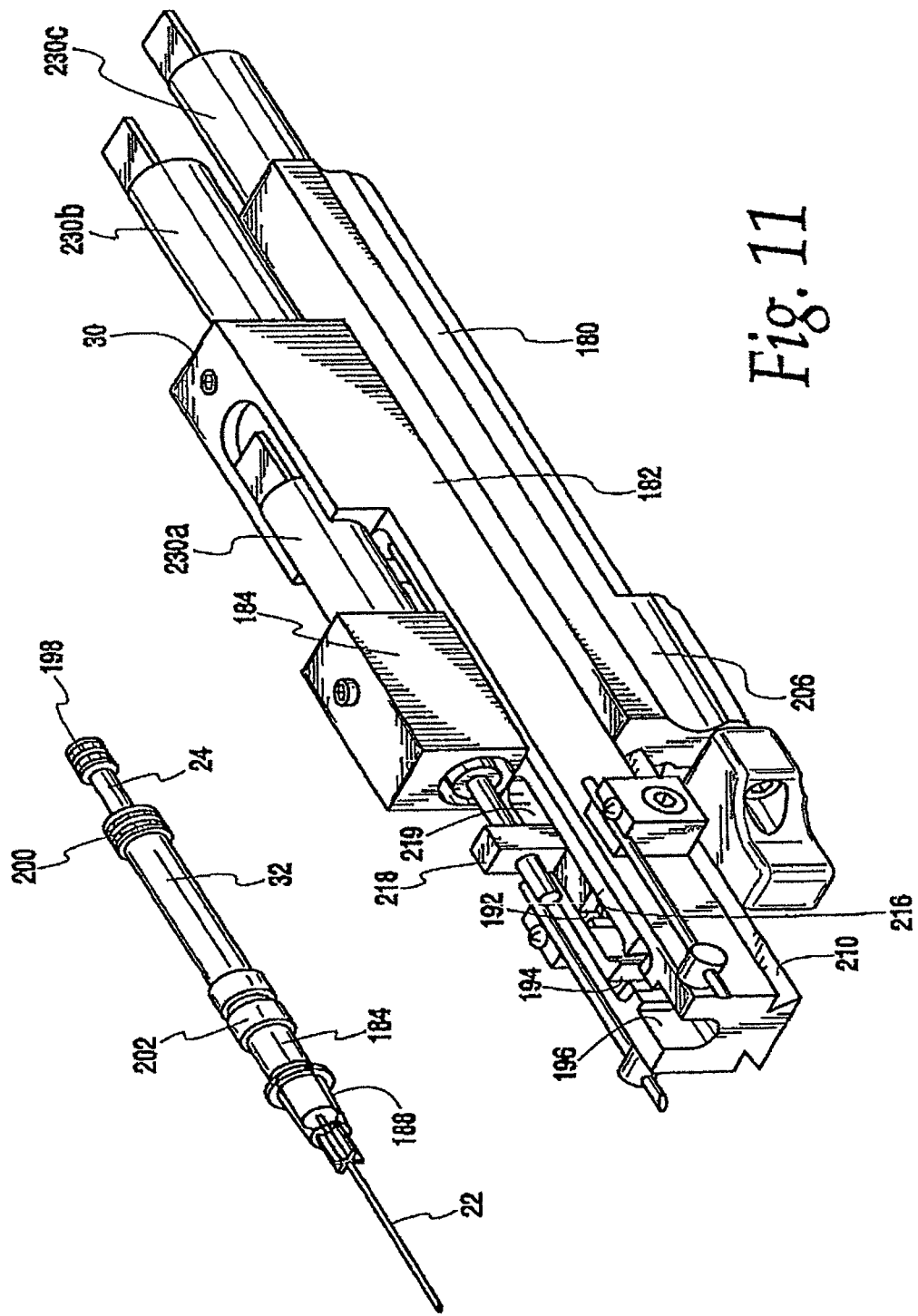
FIG. 11 is a perspective view of the implantation apparatus of FIG. 10 and the disposable needle assembly in its extended state and separated therefrom.

Another embodiment of a handheld implantation apparatus is shown in FIGS. 10-11. As in the embodiment described above, hand-held implantation apparatus 10 of FIG. 10 includes a reusable portion 30 that includes handle 180, movable block 182 and slider assembly 214. As with the embodiment of FIGS. 3-9 above, needle assembly 20, itself includes several different components that can be preassembled (as shown in FIG. 10) and are axially movable relative to one another. For example, in the embodiment shown in FIG. 10, needle assembly 20 includes plunger 32, needle adapter 184 and guidewire holder 24. Plunger 32 has a hollow cylindrical body which has an open distal end and an open proximal end. Open proximal end of plunger 32 receives guidewire 28 and guidewire holder 24.

As further shown in FIG. 10, distal end of plunger 32 is received by hollow needle adapter 184 and needle adapter 184 receives disposable needle 22. Needle 22 includes a distal piercing end and a hub 188 which is fitted over needle adapter 184. Once assembled, guidewire extends from guidewire holder 24 through plunger 32, through needle adapter 184 and needle 22. In the embodiments of FIG. 10, channel 26 is typically placed on guidewire 28 near the distal end thereof within hollow needle 22.

Needle assembly 20 is mounted onto reusable handheld portion 30. More particularly, as shown in FIG. 3, needle assembly is fitted into slots 192, 194 and 196 of implantation apparatus 30. For example, collar 198 of guidewire holder 24 is received within slot 192, collar 200 of intermediate tube 32 is positioned within slot 194, and collar 202 of needle adapter 34 is received within slot 196.

Implantation apparatus 10 includes a handle 180. Handle 180 preferably includes groove 206 along the side wall for easy gripping by the surgeon. As shown in FIGS. 10 and 11, handle 204 supports movable slider block 182. Block 182 includes a slide 210 that fits within a central slot of handle 180. During use of implantation apparatus 10, block 182 may move axially within the slot of handle 180. Movable slider block 182 may also include a slot 212 (see FIG. 10) which receives plunger block assembly 214. As shown in the figures, plunger block 214 may be slidable within block 182. Plunger block assembly 214 includes forwardly extending arms 216 which defines at its distal end a slot 192 (in which collar 25 of guidewire holder 24 is received). Plunger block assembly also includes guidewire slider block 218 that is movable within slot 219 defined by arms 216. Guidewire slider block 218 is coupled to motor 230 (discussed below) by screw 220.

Reusable portion 30 of handheld implantation apparatus 10 generally depicted in FIGS. 10 and 11 may further include drivers for selectively actuating movement of the component parts of needle assembly 20, such as needle 22, guidewire 28, plunger 32, and channel 26. As in the embodiment of FIGS. 3-9, in the embodiment of FIGS. 10 and 11, the drivers for selectively moving these and other components may be one or more motors, such as gear or stepper motors. Motors 230 may be selectively activated to move the desired component of apparatus 10. In one non-limiting example shown in FIGS. 10 and 11, a plurality of stepper motors 230(a), (b) and (c) are carried by handheld implantation apparatus. Motors 230(a)-(c) may be selectively activated by switches on the apparatus itself, remote hand-operated switches, a foot-operated controller and/or an automatically controlled via a preprogrammed controller (i.e., computer) 8.

Regardless of the means of control, in the example shown in FIGS. 10 and 11, motor 230(a) causes movement of guidewire slider block 218. Movement of guidewire slider block 218 which holds collar 25 of guidewire holder 24 results in selective back and forth movement of guidewire 28. Motor 230(b) moves arm 216 within slot 212 which holds collar 200 of plunger 32, allowing for back and forth movement of plunger 32. Finally, motor 230(c) drives block 182 including the entire needle assembly 20 further including block 214 and its associated components.

Figure 12:
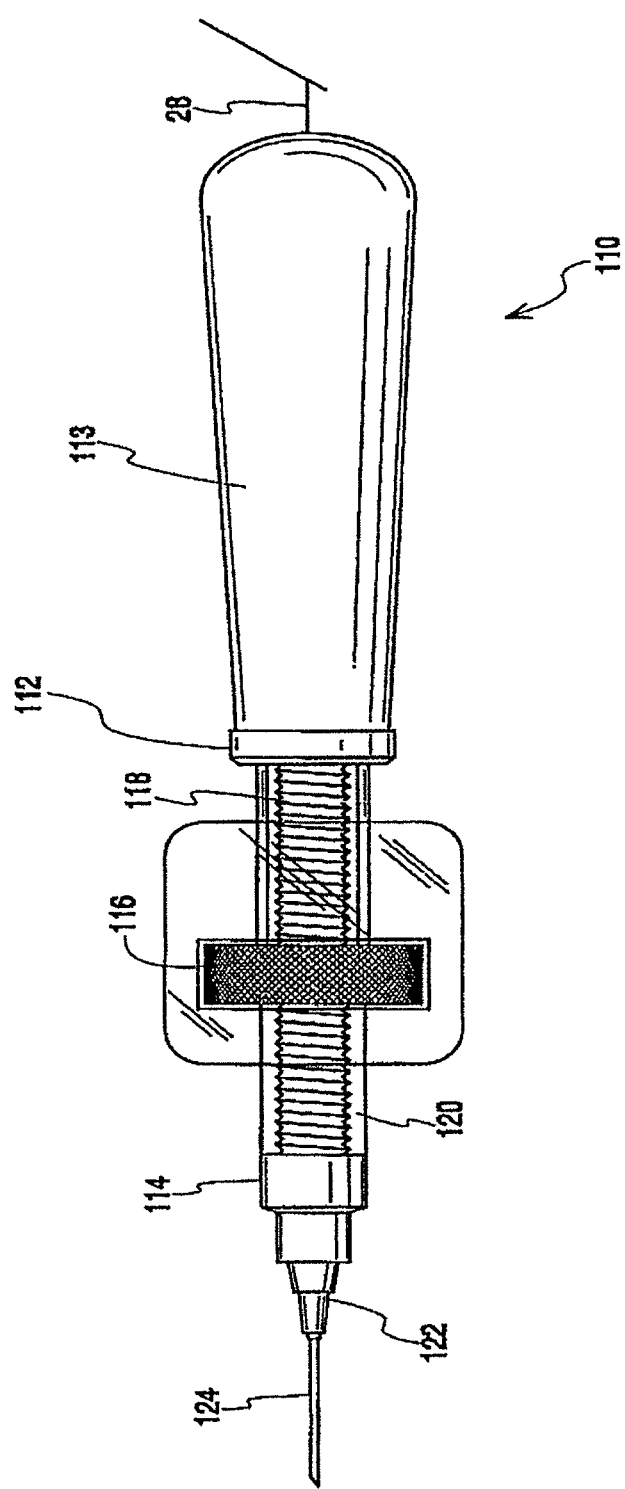
FIG. 12 is a side view of another embodiment of a handheld and manually operated implantation apparatus.

Of course, as described in relation to the embodiment of FIGS. 10-11, means for advancing or moving the operative components of handheld implantation apparatus 30 of FIGS. 11-12 need not be electrical and/or motor driven. Other embodiments of a handheld apparatus 10 that include other ways for actuating movement of the individual components may also be employed. For example, as shown in FIGS. 12-15, in alternative embodiments of a handheld implantation apparatus, the apparatus 10 may include mechanical means for selectively advancing the component parts of the needle assembly and the handheld implantation apparatus.

Turning to FIG. 12, implantation apparatus 110 includes a reusable handheld portion 112 that receives a disposable needle assembly 114. Implantation apparatus 110 includes a thumbwheel 116 placed on and movable along threaded screw 118. Attached to thumbwheel 116 is a syringe body 120. Distal end of syringe 120 receives needle assembly 122. Implantation apparatus 110 includes a conduit that extends through the handle 113 and is adapted for receiving guidewire 28.

Placement of channel 26 onto guidewire 28 may be achieved by turning thumbwheel 116 in a first direction to retract needle assembly 122 and hollow needle 124, thereby revealing the distal end of guidewire 28 and plunger tube 32. At that point, channel 26 is placed (typically manually) on guidewire 28 so that the proximal end thereof (the end opposite the leading end of channel 26) of channel comes into contact with the distal end of plunger 32. Thumbwheel 116 is then turned in an opposite direction to the first direction to slide needle 124 over plunger tube 32 and channel 26.

Channel 26 is now ready for implantation. During the implantation process, needle 124 is inserted into the eye and, more specifically, the cornea 19 or surgical limbus 17 of the eye in the manner described above and in U.S. Pat. No. 6,544,249. Needle 124 is advanced across anterior chamber 16 and into the sub-conjunctival space 18, stopping short of the conjunctiva 14. Thumbwheel 116 is then rotated again in the first direction to retract needle 124 and thereby expose channel 26. Once in place, guidewire is retracted, releasing microfistula 26 from guidewire 28. Retraction of guidewire may be achieved manually by a simple pulling of guidewire 28 at the proximal end of apparatus 110. Once channel 26 is in its final position, needle 124 is removed.

Figure 13:
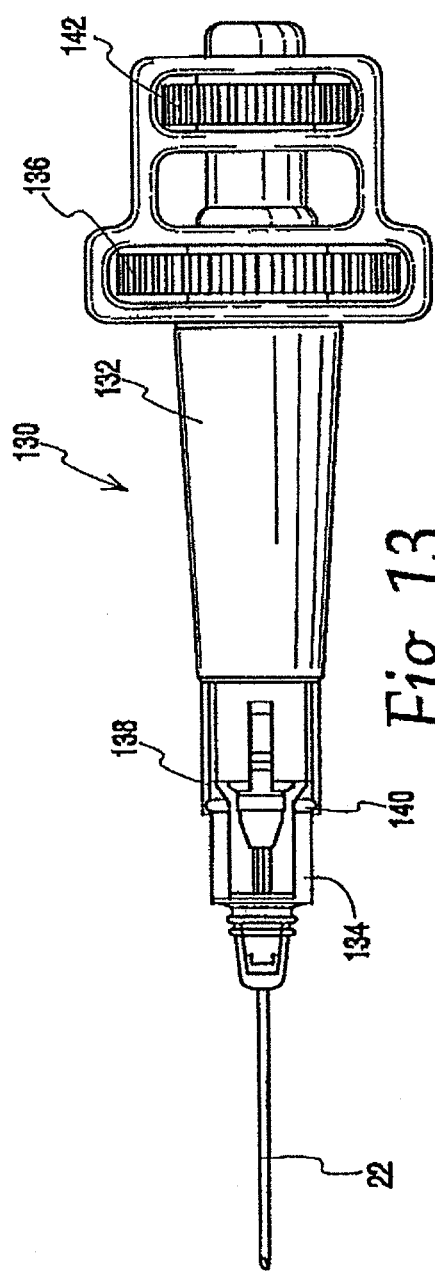
FIG. 13 is a side view of still another embodiment of a handheld and manually operated implantation apparatus.
Figure 14:
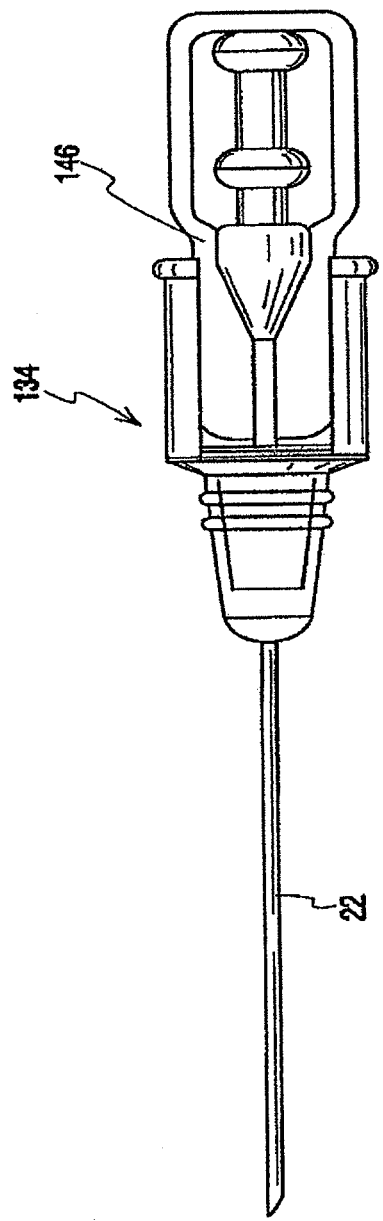
FIG. 14 is an enlarged side view of the needle assembly of the apparatus of FIG. 13.

FIGS. 13 and 14 illustrate another embodiment of a handheld implantation apparatus 130 that likewise utilizes mechanical means for advancing and/or selectively moving the component parts of the needle assembly and/or apparatus 130. As in the embodiment of FIG. 12, handheld implantation apparatus relies on mechanically driving the component parts. As shown in FIG. 13, implantation apparatus 130 includes handle portion 132 with a needle assembly 134 attached to the distal end of body 132. A thumbwheel 136 is rotatable and coupled to an internal screw (not shown). Internal screw is attached to arms 138 which grasp flange 140 of needle assembly 134, such that turning of thumbscrew 136 effects axial movement of needle assembly 134.

In contrast to the embodiment of FIG. 12, implantation apparatus 130 may further include additional means for controlling movement of other components of the implantation apparatus. For example, in the embodiment of FIG. 13, a second thumbwheel 142 is mechanically coupled to guidewire 28. A rotation of thumbwheel 142 allows for retraction of guidewire 28 after implantation of channel 28.

FIG. 14 provides an enlarged view of needle assembly 134 shown in FIG. 13. As seen in FIG. 14, an assembly retainer 146 is provided. Assembly retainer 146 is affixed to the needle assembly 134 during shipment to prevent movement of guidewire 28 and control tube. Retainer is removed prior to insertion of the needle assembly 134 onto the handle 132 of apparatus 130.

FIG. 15 shows another embodiment of an implantation apparatus. The implantation apparatus 150 of FIG. 8 includes a handle 152, a movable or slidable syringe portion 154 and a trigger 156 for actuating movement of slidable syringe 124. Implantation apparatus 150 further includes an attachable needle assembly 158 (with needle 22) at the distal end of syringe 154. As shown in FIG. 15, guidewire 28 extends through implantation apparatus 150 in similar fashion to the apparatus of FIG. 12. Guidewire 28 extends through barrel 154 and carries a tube 32 near its distal end. Barrel 154 is preferably filled with gas (e.g., air, $CO_2$, nitrogen or liquid (e.g., water, trypan blue, saline or a viscoelastic solution).

For placement of channel 26 onto guidewire 28, trigger 156 is pulled, resulting in rearward movement of syringe 154 and needle 22. Rearward movement of needle 22 exposes guidewire 28 and allows for placement of channel 26 onto guidewire. Release of the trigger 158 advances needle 22 to cover guidewire 28 and channel 26. As in the previous embodiments, needle 22 pierces cornea 19 or surgical limbus 17, and is advanced through anterior chamber 16 to the desired location of the eye (i.e. the area between the sub-conjunctival space 18 and the anterior chamber). Trigger 156 is once again pulled to move needle assembly 158 in a rearward direction thereby exposing channel 26 carried by guidewire 28. Once the surgeon has determined that the channel 26 is in the desired location, guidewire 28 is retracted, thereby releasing channel 26. As shown in FIG. 15, retraction of guidewire 28 may be performed manually, as in the embodiment of FIG. 12, by simply pulling guidewire 28. Alternatively, mechanical means for moving guidewire, as in the examples of FIGS. 12 and 13, may also be provided.

Although selective movement of guidewire 28, needle assembly, plunger 32 or guidewire holder 24 with the channel 26 using electrical, mechanical or even some manual means have been described, other means for actuating movement of these components may also be used instead of or in addition to such means. For example, movement of the various component parts may be achieved by pneumatic control or fluidic control.

The method of implanting channel 26 using implantation apparatus will now be described. The method will be described with particular reference to the embodiment of FIGS. 3-9, although many of the steps described may also be employed using other embodiments of the implantation apparatus. In addition, depending on the type of apparatus and type of channel used, there may be variations to some of the method steps. For example, in some embodiments, a guidewire may be omitted. In addition, the advancement and retraction steps of the parts of needle assembly may be continuous or incremental. Regardless of the apparatus used, the sequence of steps, distances traveled and continuous or incremental movement, the ultimate location of channel 26 is substantially the same using any of the methods, systems and apparatus described herein.

At the outset, it will be appreciated that the implantation of channel 26 requires precise placement of the channel 26 in the correct location within the eye. Moreover, it will also be appreciated that the distances traveled by the channel 26, plunger 32, guidewire 28 and needle 22 are typically measured in millimeters. Such precision may be difficult for even the most skilled surgeon to achieve by manual manipulation (due to natural hand tremors in humans). Accordingly, in embodiments other than the manual hand-held implanters in FIGS. 12-15, many of the actual implantation steps are preferably carried out under the automatic control of an external, preprogrammed controller 8. While the initial eye entry steps and some repositioning steps may be performed manually by the surgeon, steps related to the release and location of channel 26 may be automatically controlled.

In a first step, preferably performed during factory assembly, channel 26 is loaded into needle assembly 20. During loading, the distal tip of guidewire preferably extends slightly beyond the beveled tip of hollow needle 22. Channel 26 may be manually placed on guidewire 28 until proximal end of channel 26 contacts the distal end of plunger 32. Guidewire 28, with channel 26 placed thereon is then retracted into hollow needle 22.

Prior to loading needle assembly 20 into apparatus 30, pre-positioning of arm-subassembly may be desired or required. Thus, in a first step, all motors are activated to retract guidewire arm 54, plunger arm 58 and needle arm 62 to a proximal most position such that the proximal end surfaces of the arms abut against collars 53. This "hard stop" position is shown schematically in FIG. 9*a*. The operator may then prepare implantation apparatus 30 for loading of needle assembly by activating each motor and advancing each arm assembly 55 to a "home" position and shown in FIG. 9(*b*). As will be seen in FIG. 9(*b*) movement of needle arm 62 is restricted by wall 70 of apparatus 30. With the motors properly aligned in the "home" position, needle assembly is installed by inserting guidewire hub block 86 into guidewire hub slot 57; plunger hub block 90 into plunger hub slot 59 and needle hub block into slot 63. With needle assembly 20 properly installed, the surgeon may begin the procedure by inserting the end distal tip of hollow needle 22 into the eye. As shown in FIG. 1 and as previously described, the surgeon inserts the hollow needle 22 into the anterior chamber via the cornea or surgical limbus of the eye and advances it either manually (or under automatic control) to a location short of the final implantation site. Alternatively, the surgeon may first make an incision in the eye and insert needle 22 through the incision. Once the needle 22 has been properly inserted and placed, the program may be activated to commence automatic implantation of channel 26. In a first implantation step, simultaneously motors) 44 and 46 are activated to advance guidewire arm 54 and plunger are 58 as shown in FIG. 9(*c*) which thereby advances channel 26 forward into the subconjunctival space of the eye, as generally depicted in FIG. 9(*c*). For example, in one embodiment, plunger 32 and guidewire 28 are advanced approximately a total of 2 millimeters. Preferably, the rate of placement of channel is carefully controlled because it allows the channel to absorb fluid from the surrounding tissue thereby causing it to swell and to provide better anchoring in the tissue. Rapid advancement or placement of microfistula channel 26 may not allow tube 26 to adequately swell which can possibly result in unwanted migration of channel 26 after implantation. In one embodiment, the rate of placement may be between approximately 0.25-0.65 mm/sec.

After the advancement of the plunger and guidewire described above, motor 48 is activated and needle arm 62 is moved in a rearward direction such that needle 22 is withdrawn from its position shown in FIG. 9(*c*) to the position shown in FIG. 9(*d*). Withdrawal of needle 22 should preferably expose the entire length of channel 26, and, in addition, the distal end of the plunger, thereby allowing the surgeon to visualize the final position of the proximal edge of the channel. In one embodiment, the distance that hollow needle 22 is withdrawn is approximately 4.2 millimeters. At this point, the program prompts (e.g., audibly) the surgeon to visually view the location of channel 26 and determine if it is correctly placed. The surgeon can manually make any adjustments to a desired position by moving the implanter forward or backward. The automatic system may be programmed to allow the surgeon sufficient time to make any further manual adjustments and may require the surgeon to press the foot or other switch or otherwise effect movement to continue delivery of the channel. After a selected period of time, the automated program preferably resumes control of implantation procedure by activating motor guidewire motor 44, to retract guidewire arm 54 and thus withdraw guidewire 28 as shown in FIG. 9(*e*). Removal of the guidewire preferably occurs in one single step as shown in FIG. 9(*e*). Finally, the system will then preferably alert the surgeon that the procedure is now complete and the needle 22 may be withdrawn (manually or automatically) from the eye as shown in FIG. 9(*f*).

From the preceding discussion, it will be appreciated that bioabsorbable microfistula channel is implanted by directing the needle across the anterior chamber, entering the trabecular meshwork (preferably between Schwalbe's Line and the Scleral spur), and directing the needle through the sclera until the distal tip of the needle is visible in the subconjunctival space. The length of the channel through the sclera should be approximately 2-4 mm. Once the surgeon has placed the needle in this location, he may actuate the implanter to begin the release steps. The channel is released and the needle is withdrawn such that approximately 1-2 mm of the channel resides in the sub conjunctival space, approximately 2-4 mm resides in the scleral channel, and approximately 1-2 mm resides in the anterior chamber. Once the channel is released, the surgeon removes apparatus needle 20.

Proper positioning of the bioabsorbable channel 26 should be carefully controlled for at least the following reasons. If the surgical procedure results in the formation of a bleb, the more posterior the bleb is located, the fewer complications can be expected. Additionally, the bleb interferes less with eyelid motion and is generally more comfortable for the patient. Second, a longer scleral channel provides more surface contact between the channel and the tissue providing better anchoring. Third, the location of the channel may play a role in stimulating the formation of active drainage structures such as veins or lymph vessels. Finally, the location of the channel should be such so as to avoid other anatomical structures such as the ciliary body, iris, and cornea. Trauma to these structures could cause bleeding and other complications for the patient. Additionally, if the bleb is shallow in height and diffuse in surface area, it provides better drainage and less mechanical interference with the patient's eye. Tall, anteriorly located blebs are more susceptible to complications such as conjunctival erosions or blebitis which require further intervention by the surgeon.

The ab interno approach provides better placement than the ab externo approach because it provides the surgeon better visibility for entering the eye. If directing the needle from an ab externo approach, it is often very difficult for the surgeon to direct the needle to the trabecular meshwork (between Schwalbe's line and the scleral spur) without damaging the cornea, iris, or ciliary body.

In an alternative method of implantation, it is possible to direct the needle from the trabecular meshwork into the suprachoroidal space (instead of the subconjunctival space) and provide pressure relief by connecting these two spaces. The suprachoroidal space also called supracilliary space has been shown to be at a pressure of a few mmHg below the pressure in the anterior chamber.

Common to all of the embodiments of handheld implantation apparatus are a needle assembly including a hollow needle. In a preferred embodiment, hollow needle 22 may be any needle suitable for use in medical procedures. As such, needle 22 is made of a hard and rigid material such as stainless steel with a beveled sharpened distal tip. Needle 22 is bonded, welded, overmolded, or otherwise attached to the needle mount 23 and/or hub that is adapted for placement onto the distal end of a needle assembly. The needle 22 is disposable and intended for one time use.

Figure 19:
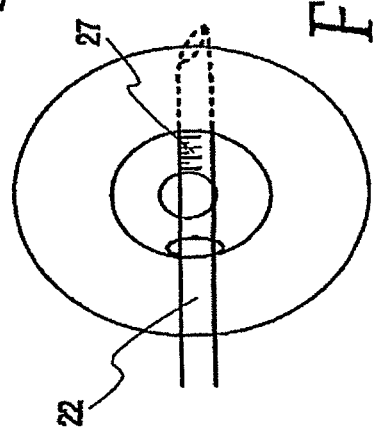
FIG. 19 is a front view of a graduated needle inserted into the eye of a patient.

Hollow needle 22 and indeed, the entire needle assembly may be sterilized by known sterilization techniques such as autoclaving, ethelyne oxide, plasma, electron beam, or gamma radiation sterilization. In a preferred embodiment, needle 22 is a 25 gauge thin walled needle that is commercially available from Terumo Medical Corp., Elkton, Md. 21921. The inside diameter of hollow needle 22 must be sufficient to accommodate optional guidewire 28, channel 26 and plunger tube 32, with an inner diameter of 200-400 μm being preferred. The usable length of needle 22 may be anywhere between 20-30 mm, although a length of approximately 22 mm is typical and preferred. Preferably, needle 22 may include markings or graduations 27 near the distal tip as shown in FIG. 19. A graduated needle may be particularly useful to a surgeon inasmuch as much of the needle within the eye is not visible to the surgeon. Typically, the only visible portion of needle 22 is the portion within the anterior chamber. Accordingly, graduations 27 uniformly spaced along the needle shaft assist the surgeon in determining how far to advance the needle in order to place channel 26 in the desired location. In one embodiment, the graduations may be applied using laser marks, ink, paint or engraving and are typically spaced 0.1 to 1.0 mm apart.

While a straight hollow needle of the type typically used in medial procedures is generally preferred, in an alternative to the needle shown in the FIGS. 3-15 and described above, needle 22 may be rigid and have a distal portion that is arcute as shown in FIGS. 22-24. As shown in FIGS. 22(a)-(d) and FIGS. 23-24 arcuate needle may be preferably U-shaped or substantially U-shaped. With an "arcuate" needle, instead of pushing the needle into the patient's eye, the surgeon may orient the needle to "pull" the needle into the patient's eye. As shown in FIGS. 23-24, the distal portion of the needle 22 terminating in the beveled tip, identified by reference number 96 is preferably disposed obliquely relative to the longitudinal axis of needle shaft 98 as seen in FIG. 24.

Providing a piercing end 96 that is bent away from the plane of needle shaft 98 can facilitate manipulation and rotation of needle 22 during implantation of tube 26. It may also provide the surgeon with greater flexibility in terms of selecting the corneal entry site and the ultimate final position of channel 26. This is perhaps best seen with reference to FIGS. 20, 21 and 22(a)-(d).

Figure 20:
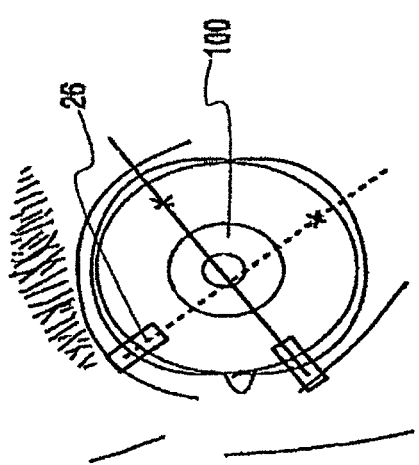
FIG. 20 is a front view showing a transpupil channel insertion and placement.

For example, FIG. 20 depicts a transpupil implantation delivery generally described in U.S. Pat. No. 6,544,249 as shown in FIG. 1. While the approach is satisfactory, it does require the needle to cross the visual axis. In the event of a surgical error that causes damage to the cornea or lens, corrective surgery may be required.

Figure 21:
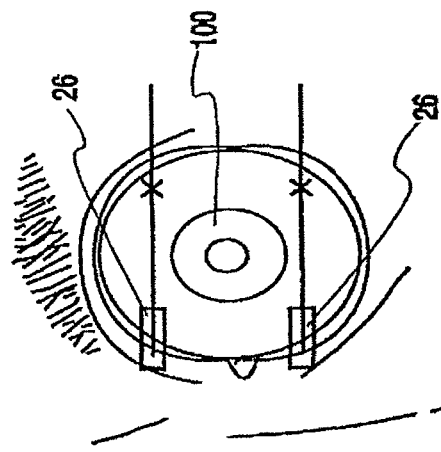
FIG. 21 is a schematic view showing an ipsilateral tangential channel insertion and placement.

FIG. 21 depicts an alternative method of delivery referred to as an ipsilateral tangential delivery of channel 26. In the ipsilateral tangential delivery method, the straight needle is directed tangentially to the pupil 100 border and the surgical limbus. This type of implant delivery allows the channel to be delivered to a greater circumference of the eye and has the advantage of avoiding the visual axis. Avoiding the visual axis reduces the risk of complications to the cornea 19 and lens through contact during surgery. Ipsilateral tangential delivery is a modification of the transpupil implant location generally described in U.S. Pat. No. 6,544,249, previously incorporated by reference.

Although the transpupil implant delivery and/or the ipsilateral tangential delivery, if performed correctly, are acceptable methods of delivering channel 26, they do somewhat limit the location of the corneal entry site due to interference with the nose and eye orbit bones. In that regard, an arcuate needle of the type described above and shown in FIGS. 22(a)-(d) and FIGS. 23-24 may provide greater flexibility to the surgeon. With an arcuate needle, channel 26 may be placed anywhere around the 360.degree. circumference of the eye, including the temporal quadrants which would not be otherwise accessible for the reasons discussed above.

A further advantage of the arcuate needle and the delivery implant method associated therewith is that microfistula channel 26 can be delivered without crossing the lens i.e., visual axis, thereby reducing the risk of complications. An arcuate needle design may also allow the surgery to be done in patients with abnormal anatomy or who have previously undergone surgery.

In accordance with delivering a microfistula channel 26 using the U-shaped hollow needle 20 of FIGS. 23 and 24, as noted above, instead of pushing the needle into the patient's eye, the surgeon orients the needle to "pull" needle 22 into the patient's eye. Thus, as shown in FIG. 22(a), the pointed tip of hollow needle 22 is inserted at the desired corneal entry point and pulled in the direction of the arrow. Once the portion of needle 22 that contains the channel 26 is in the patient's eye, the surgeon rotates the needle and directs the needle 22 toward the target within the angle of the anterior chamber. After adjusting needle 22 to the proper position, the surgeon again pulls the needle 22 in the direction of the arrow of FIG. 22(b) so that the needle is directed through the trabecular mesh work and sclera. The particular advancement and delivery steps described previously are then performed to place the channel 26 in the desired location and withdraw the guidewire plunger and needle from the eye. Of course, retraction and other movements of the needle may be automatically controlled in the manner described above and as shown in FIG. 9.

In a further embodiment, a hollow needle 22 that is bent (but not necessarily in a U-shape as described above), may be provided. A needle of this type is shown in FIGS. 25-27. As with the "arcuate" or U-shaped needles discussed above, a simple bend in the distal portion of needle 22 can likewise avoid interference from the patient's facial features. A bend that creates an angle α of between 900°-180° may be preferred. Providing a needle 22 with a bend is also ergonomically desirable in that it improves the position of the surgeon's hands during surgery. For example, by providing a bend in the distal portion of needle 22, a surgeon may rest and stabilize his hands on the patient's forehead or other support while making the initial corneal entry and carrying out the later implantation steps. Providing a bend in the distal portion of needle 22 is not merely an alternative to the U-shaped needle of FIGS. 23 and 24. In fact, both features i.e., a needle with an arcuate distal portion and further having a bend near the distal tip may be employed together in the needle 22.

Whether the needle is U-shaped or bent at an angle .alpha. shown in FIG. 25, the component parts of needle 22 must likewise be susceptible to bending. Accordingly, instead of a rigid plunger 32 and guidewire 28, both the plunger and guidewire may be, in part, bendable or be made of a material that is bendable, yet provides adequate support and has adequate strength. In one example, the plunger 32 may be made of a tightly wound coil such as but limited to a spring or coil. Alternatively, at least a portion of guidewire 28 or plunger 32 may be made of a flexible plastic material including a polymeric material, examples of which include polyimide, PEEK, Pebax or Teflon. Other bendable, flexible materials may also be used. Similarly, guidewire 28 may be made of any of the above-described materials or a material such as nitinol which has shape memory characteristics. The entire plunger or guidewire 28 may be made of the flexible materials described above or, as shown in FIG. 27 only a portion of the guidewire 28 or plunger tube 32 may be made of the selected material or be otherwise bendable.

Typically, however, guidewire 28 is preferably a narrow gauge wire made of a suitable rigid material. A preferred material is tungsten or stainless steel, although other non-metallic materials may also be used. In a preferred embodiment, guidewire 28 is solid with an outside diameter of approximately 50-200 (ideally 125) microns. Where guidewire 28 is made of tungsten, it may be coated with a Teflon, polymeric, or other plastic material to reduce friction and assist in movement of channel 26 along guidewire 28 during implantation.

Channels 26 useful in the present invention, are preferably made of a biocompatible and preferably bioabsorbable material. The materials preferably have a selected rigidity, a selected stiffness and a selected ability to swell (during manufacture and/or after implantation) in order to provide for secure implantation of the channel in the desired section of the eye. Selecting a material that is capable of a controlled swelling is also desirable. By controlled swelling, it is meant that the swellable material is such that the outer diameter of the channel expands (increases) without decreasing the inner diameter. The inner diameter may increase or remain substantially the same. The materials and methods for making channels described below provide such controlled swelling. By sufficient biocompatibility, it is meant that the material selected should be one that avoids moderate to severe inflammatory or immune reactions or scarring in the eye. The bioabsorbability is such that the channel is capable of being absorbed by the body after it has been implanted for a period of anywhere between 30 days and 2 years and, more preferably, several months such as 4-7 months.

In one embodiment, the material selected for the channels is preferably a gelatin or other similar material. In a preferred embodiment, the gelatin used for making the channel is known as gelatin Type B from bovine skin. A preferred gelatin is PB Leiner gelatin from bovine skin, Type B, 225 Bloom, USP. Another material that may be used in the making of the channels is a gelatin Type A from porcine skin also available from Sigma Chemical. Such gelatin is available is available from Sigma Chemical Company of St. Louis, Mo. under Code G-9382. Still other suitable gelatins include bovine bone gelatin, porcine bone gelatin and human-derived gelatins. In addition to gelatins, microfistula channel may be made of hydroxypropyl methycellulose (HPMC), collagen, polylactic acid, polylglycolic acid, hyaluronic acid and glycosaminoglycans.

In accordance with the present invention, gelatin channels are preferably cross-linked. Cross-linking increases the inter- and intramolecular binding of the gelatin substrate. Any means for cross-linking the gelatin may be used. In a preferred embodiment, the formed gelatin channels are treated with a solution of a cross-linking agent such as, but not limited to, glutaraldehyde. Other suitable compounds for cross-linking include 1-ethyl-3-[3-(dimethylamino)propyl] carbodiimide (EDC). Cross-linking by radiation, such as gamma or electron beam (e-beam) may be alternatively employed.

In one embodiment, the gelatin channels are contacted with a solution of approximately 25% glutaraldehyde for a selected period of time. One suitable form of glutaraldehyde is a grade 1G5882 glutaraldehyde available from Sigma Aldridge Company of Germany, although other glutaraldehyde solutions may also be used. The pH of the glutaraldehyde solution should preferably be in the range of 7 to 7.8 and, more preferably, 7.35-7.44 and typically approximately 7.4.+−.0.01. If necessary, the pH may be adjusted by adding a suitable amount of a base such as sodium hydroxide as needed.

Channels used in the present invention are generally cylindrically shaped having an outside cylindrical wall and, in one embodiment, a hollow interior. The channels preferably have an inside diameter of approximately 50-250 microns and, more preferably, an inside diameter and us, a flow path diameter of approximately 150 to 230 microns. The outside diameter of the channels may be approximately 190-300 with a minimum wall thickness of 30-70 microns for stiffness.

Figure 28:
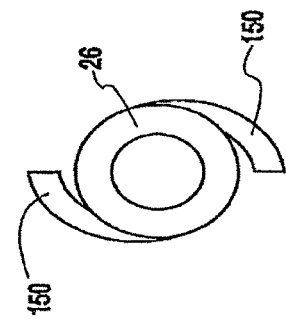
FIG. 28 is a perspective view of a cylindrical channel including a tapered end.
Figure 29:
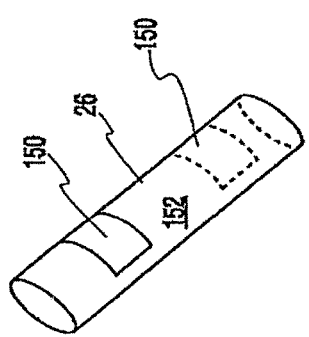
FIG. 29 is a perspective view of a cylindrical channel including retaining tabs for limiting migration of the channel.
Figure 30:
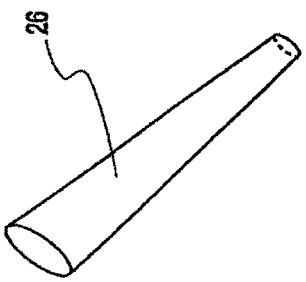
FIG. 30 is an end view of the tabbed channel of FIG. 29.
Figure 31:
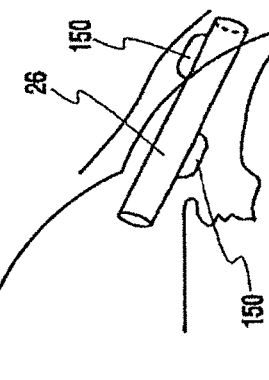
FIG. 31 is a perspective view of a cylindrical channel including centrally located barbs to limit migration of the implanted channel.
Figure 32:
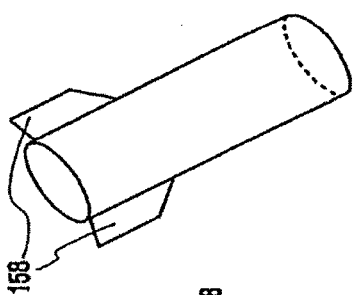
FIG. 32 is a perspective view of a cylindrical channel including barbs located at one of the implanted channel to limit migration thereof.
Figure 33:
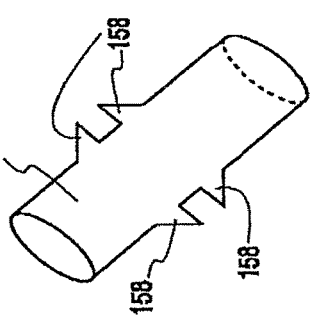
FIG. 33 shows the tabbed channel of FIGS. 29-30 inserted within the eye of the patient.

As shown in FIG. 28, one end of tube 26 may be slightly tapered to limit or prevent migration of tube 26 after it has been implanted. Other means for limiting migration are also shown in FIGS. 29-33. For example, channel 26 may include expandable tab 150 along outer surface 152 of tube 26. As shown in FIG. 29, prior to deployment and introduction of tube into the patient's eye, tabs 150 are rolled or otherwise pressed against surface 152. Tabs 150 may also be features that are cut out of the outer surface of channel 26 (i.e., not separately applied). Upon contact with an aqueous environment, tabs 150 are deployed. Specifically, contact with an aqueous environment causes tabs 150 to expand as shown in FIG. 30 and, thereby, create an obstruction which limits or prevents migration of tube 26. Tube 26 may include a plurality of tabs, typically but not limited to 1-4, and may be located nearer the subconjunctival side, the anterior chamber or both, as shown in FIG. 33. Other means for limiting or preventing migration include barbs 158 placed along the length of tube 26 as shown in FIGS. 31-32 and also disclosed in U.S. Pat. Nos. 6,544,249 and 6,007,511, previously incorporated by reference.

The length of the channel may be any length sufficient to provide a passageway or canal between the anterior chamber and the subconjunctival space. Typically, the length of the channel is between approximately 2 to 8 millimeters with a total length of approximately 6 millimeters, in most cases being preferred. The inner diameter and/or length of tube 26 can be varied in order to regulate the flow rate through channel 26. A preferred flow rate is approximately 1-3 microliters per minute, with a flow rate of approximately 2 microliters being more preferred.

In one embodiment, channels 26 may be made by dipping a core or substrate such as a wire of a suitable diameter in a solution of gelatin. The gelatin solution is typically prepared by dissolving a gelatin powder in de-ionized water or sterile water for injection and placing the dissolved gelatin in a water bath at a temperature of approximately 55° C. with thorough mixing to ensure complete dissolution of the gelatin. In one embodiment, the ratio of solid gelatin to water is approximately 10% to 50% gelatin by weight to 50% to 90% by weight of water. In an embodiment, the gelatin solution includes approximately 40% by weight, gelatin dissolved in water. The resulting gelatin solution preferably is devoid of any air bubbles and has a viscosity that is between approximately 200-500 cp and more preferably between approximately 260 and 410 cp (centipoise).

Once the gelatin solution has been prepared, in accordance with the method described above, supporting structures such as wires having a selected diameter are dipped into the solution to form the gelatin channels. Stainless steel wires coated with a biocompatible, lubricious material such as polytetrafluoroethylene (Teflon) are preferred.

Typically, the wires are gently lowered into a container of the gelatin solution and then slowly withdrawn. The rate of movement is selected to control the thickness of the coat. In addition, it is preferred that a the tube be removed at a constant rate in order to provide the desired coating. To ensure that the gelatin is spread evenly over the surface of the wire, in one embodiment, the wires may be rotated in a stream of cool air which helps to set the gelatin solution and affix film onto the wire. Dipping and withdrawing the wire supports may be repeated several times to further ensure even coating of the gelatin. Once the wires have been sufficiently coated with gelatin, the resulting gelatin films on the wire may be dried at room temperature for at least 1 hour, and more preferably, approximately 10 to 24 hours. Apparatus for forming gelatin tubes are described below.

Once dried, the formed microfistula gelatin channels are treated with a cross-linking agent. In one embodiment, the formed microfistula gelatin films may be cross-linked by dipping the wire (with film thereon) into the 25% glutaraldehyde solution, at pH of approximately 7.0-7.8 and more preferably approximately 7.35-7.44 at room temperature for at least 4 hours and preferably between approximately 10 to 36 hours, depending on the degree of cross-linking desired. In one embodiment, formed channel is contacted with a cross-linking agent such as gluteraldehyde for at least approximately 16 hours. Cross-linking can also be accelerated when it is performed a high temperatures. It is believed that the degree of cross-linking is proportional to the bio-absorption time of the channel once implanted. In general, the more cross-linking, the longer the survival of the channel in the body.

The residual glutaraldehyde or other cross-linking agent is removed from the formed channels by soaking the tubes in a volume of sterile water for injection. The water may optionally be replaced at regular intervals, circulated or re-circulated to accelerate diffusion of the unbound glutaraldehyde from the tube. The tubes are washed for a period of a few hours to a period of a few months with the ideal time being 3-14 days. The now cross-linked gelatin tubes may then be dried (cured) at ambient temperature for a selected period of time. It has been observed that a drying period of approximately 48-96 hours and more typically 3 days (i.e., 72 hours) may be preferred for the formation of the cross-linked gelatin tubes.

Where a cross-linking agent is used, it may be desirable to include a quenching agent in the method of making channel 26. Quenching agents remove unbound molecules of the cross-linking agent from the formed channel 26. In certain cases, removing the cross-linking agent may reduce the potential toxicity to a patient if too much of the cross-linking agent is released from channel 26. Formed channel 26 is preferably contacted with the quenching agent after the cross-linking treatment and, preferably, may be included with the washing/rinsing solution. Examples of quenching agents include glycine or sodium borohydride.

The formed gelatin tubes may be further treated with biologics, pharmaceuticals or other chemicals selected to regulate the body's response to the implantation of channel 26 and the subsequent healing process. Examples of suitable agents include anti-mitolic pharmaceuticals such as Mitomycin-C or 5-Fluorouracil, anti-VEGF (such as Lucintes, Macugen, Avastin, VEGF or steroids).

After the requisite drying period, the formed and cross-linked gelatin tubes are removed from the underlying supports or wires. In one embodiment, wire tubes may be cut at two ends and the formed gelatin tube slowly removed from the wire support. In another embodiment, wires with gelatin film thereon, may be pushed off using a plunger or tube to remove the formed gelatin channel.

FIGS. 16 and 17 show two alternative methods and apparatus for forming gelatin channels. In FIG. 16, apparatus 140 includes a suspended wire 142 that may be introduced into a vacuum chamber 144 at a temperature of 20° C. The gelatin solution 146 maintained at 55° C. may be applied to the wire in vacuum chamber 144 by spraying via air jet 148. Wire 142 is rotated by rotating apparatus 150 to ensure that the sprayed gelatin is applied evenly to the surface of wire 142.

In FIG. 17, a further alternative embodiment of forming gelatin tubes is shown. In accordance with the embodiment of FIG. 17, a wire 142 attached to a rotating apparatus 150 is dipped into the gelatin solution 163 at 55° C. as generally described above. Wire 142 is dipped into and removed, from the gelatin solution repeatedly and sprayed with air to ensure an even coat of the gelatin film onto the wire. In either embodiment of FIGS. 16 and 17, the gelatin tubes formed thereby may be further subjected to a cross-linking step desired above.

The gelatin tube may also be formed by preparing the mixture as described above and extruding the gelatin into a tubular shape using standard plastics processing techniques. Preparing channel 26 by extrusion allows for providing channels of different cross sections. For example, as shown in FIG. 34, channels 26 having two or more passageways 260 may be provided, allowing for flow regulation. In one embodiment, passageways 260 may be selectively opened or obstructed, as shown in the shading on FIG. 34(d) to selectively control flow therethrough. One of the passageways 260 may be adapted to receive guidewire 28 or, in the alternative, channel 26 of FIG. 34 may be used (and implanted) without a guidewire, as previously described. Channel 26 shown in FIG. 34 may also provide greater structural integrity after implantation.

Figure 18:
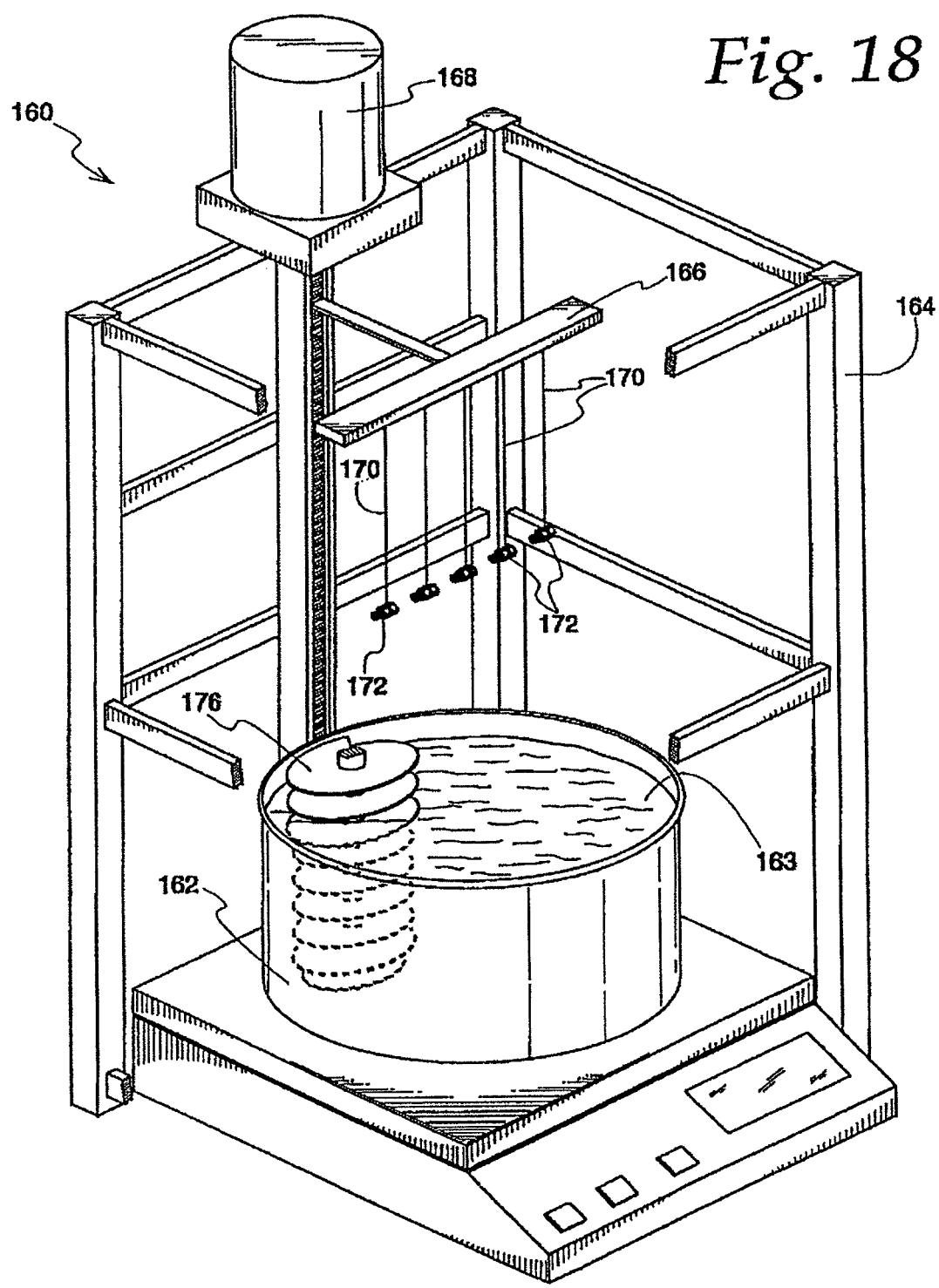
FIG. 18 is a perspective view of an apparatus for making a plurality of microfistula gelatin tubes.

FIG. 18 shows an automated apparatus 160 for preparing a plurality of microfistula gelatin tubes. Shown in FIG. 18 is an apparatus 160 that includes a temperature controlled bath 162 of the gelatin solution 163. The apparatus includes a frame 164 that carries a vertically movable dipping arm 166. The dipping arm is coupled to a gear box 168 which is actuated by a rotary motor. The dipping arm includes a plurality of clamps (not shown) for holding several mandrel wires 170 for dipping into the gelatin solution. As further shown in FIG. 18, mandrel wires 170 may further include weights 172 suspended at their distal ends to ensure that the wire remains substantially straight (without kinking or curving) and to dampen oscillations or vibrations when being dipped in the gelatin solution 163. The operation of apparatus 160 may be controlled by a controller such as a computer with commands for dipping and withdrawal of the wires from the gelatin solution. A stirrer 176 may be provided to ensure the consistency of the gelatin solution. After the gelatin tubes have been formed, the tubes are dried and cross-linked as described above.

Channels 26 made in accordance with the methods described above, allow for continuous and controlled drainage of aqueous humor from the anterior chamber of the eye. The preferred drainage flow rate is approximately 2 microliters per minute, although by varying the inner diameter and length of channel 26, the flow rate may be adjusted as needed. One or more channels 26 may be implanted into the eye of the patient to further control the drainage.

In addition to providing a safe and efficient way to relieve intraocular pressure in the eye, it has been observed that implanted channels disclosed herein can also contribute to regulating the flow rate (due to resistance of the lymphatic outflow tract) and stimulate growth of functional drainage structures between the eye and the lymphatic and/or venous systems. These drainage structures evacuate fluid from the subconjunctiva which also result in a low diffuse bleb, a small bleb reservoir or no bleb whatsoever.

The formation of drainage pathways formed by and to the lymphatic system and/or veins may have applications beyond the treatment of glaucoma. Thus, the methods of channel implantation may be useful in the treatment of other tissues and organs where drainage may be desired or required.

In addition, it has been observed that as the microfistula channel absorbs, a "natural" microfistula channel or pathway lined with cells is formed. This "natural" channel is stable. The implanted channel stays in place (thereby keeping the opposing sides of the formed channel separated) long enough to allow for a confluent covering of cells to form. Once these cells form, they are stable, thus eliminating the need for a foreign body to be placed in the formed space.

While the methods, apparatus and systems of this disclosure have been described with reference to certain embodiments, it will be apparent to those skilled in the art that numerous modifications and variations can be made within the scope and spirit of the inventions as recited in the appended claims.

What is claimed is:

1. A system for deploying an intraocular shunt, the system comprising:
    a deployment device and an intraocular shunt carried by the deployment device, the device comprising:
        a housing; and
        a deployment mechanism at least partially disposed within the housing and comprising a plunger component, a plunger coupled to a distal segment of the plunger component, a plunger arm, a shaft component, a hollow shaft coupled to the shaft component, a shaft arm, and a longitudinal axis, the plunger component comprising a proximal segment and a plunger pin protruding radially from the proximal segment, the plunger arm comprising a plunger hub slot configured to receive a coupling portion of the plunger component for coupling the plunger component to the plunger arm, the shaft component comprising a proximal segment and a shaft pin protruding radially from the shaft component proximal segment, the shaft arm comprising a shaft hub slot configured to receive a coupling portion of the shaft component for coupling the shaft component to the shaft arm;
        wherein the shaft is coupled to the deployment mechanism such that the plunger is slidable along the axis within the shaft, wherein the shaft is configured to hold the shunt, and
        wherein the deployment mechanism is configured (i) to advance the shunt along the axis within the shaft by pushing the shunt with the plunger, without moving the shaft, to a partially exposed position in which a proximal portion of the shunt is disposed within the shaft and a distal portion of the shunt is disposed beyond a distal end of the shaft, and then, (ii) while a longitudinal position of the shunt is substantially maintained along the axis, relative to the housing, by the plunger, to retract the shaft such that the distal end of the shaft is retracted proximally of the shunt proximal portion.

2. The system according to claim 1, wherein a distal end of the shaft is beveled.

3. The system according to claim 1, wherein the hollow shaft is a needle.

4. The system according to claim 1, wherein the shaft is removable from the deployment mechanism.

5. The system according to claim 1, wherein the deployment mechanism includes a stopper that limits longitudinal movement of the shaft along the axis.

6. The system according to claim 1, wherein the shunt comprises: a hollow channel defining an inlet configured to receive fluid from an anterior chamber of an eye, and an outlet configured to direct the fluid to a location of low pressure with respect to the anterior chamber; the hollow channel comprising an outer surface that is expandable.

7. The system according to claim 6, wherein the hollow channel is bioabsorbable.

8. The system according to claim 6, wherein said hollow channel defines a flow path extending from the inlet to the outlet and that remains substantially constant as the outer surface expands.

9. The system according to claim 6, wherein the shunt comprises a cross-linked gelatin.

10. The system according to claim 6, further comprising at least one member on the outer surface that assists in retaining the shunt in the eye.

11. The system according to claim 1, wherein the shunt comprises: a hollow channel defining a flow path and having an inlet configured to receive fluid from an anterior chamber of an eye and an outlet configured to direct the fluid to a location of low pressure with respect to the anterior chamber, wherein the channel further comprises a variable inner diameter.

12. The system according to claim 11, wherein the inner diameter increases along the length of the channel from the inlet to the outlet.

13. The system according to claim 11, wherein the inner diameter continuously increases along the length of the channel.

14. The system according to claim 11, wherein the inner diameter remains constant along portions of the length of the channel.

15. The system according to claim 11, further comprising at least one member on an outer surface of the channel that assists in retaining the shunt in the eye.

16. The system according to claim 1, wherein the deployment mechanism is further configured such that the shunt is positioned adjacent the distal end of the shaft prior to operation of the deployment mechanism.

17. The system according to claim 1, wherein the shaft is configured to hold the shunt with the shaft distal end extending beyond the shunt distal portion.

18. The system according to claim 1, wherein the shaft and plunger pins constrain movement of the shaft component and the plunger component such that the shaft and the plunger are longitudinally movable along the axis relative to the housing.

19. The system according to claim 1, wherein the shaft and plunger pins constrain radial movement of the shaft component and the plunger component.

20. The system according to claim 19, wherein the shaft and plunger pins are configured to contact an inner surface of the housing to maintain longitudinal alignments of the coupling portions of the shaft component and the plunger component along the axis.

21. The system according to claim 1, further comprising a plunger motor coupled to the plunger arm for longitudinally moving the plunger along the axis and a shaft motor coupled to the shaft arm for longitudinally moving the shaft along the axis.

22. A method for deploying a shunt into an eye, the method comprising:
providing a system for deploying an intraocular shunt, the system comprising:
a deployment device comprising: a housing; a deployment mechanism at least partially disposed within the housing and comprising a plunger and a longitudinal axis; and a hollow shaft coupled to the deployment mechanism such that the plunger is slidably disposed within the shaft along the axis, wherein the shaft is configured to hold an intraocular shunt;
inserting the system into an eye;
advancing the plunger along the axis to move the shunt to a partially exposed position in which a proximal portion of the shunt is disposed within the shaft and a distal portion of the shunt is disposed beyond a distal end of the shaft; and
after advancing the shunt to the exposed position, and while substantially maintaining a longitudinal position of both the plunger and the shunt along the axis, relative to the housing, retracting the distal end of the shaft proximally of the shunt proximal portion to release the shunt from the shaft of the deployment device.

23. The method according to claim 22, wherein the shunt is deployed such that an inlet receives fluid flow from an anterior chamber of the eye and an outlet directs flow to a location of low pressure with respect to the anterior chamber.

24. The method according to claim 23, wherein the location is selected from the group consisting of: the subconjunctival space, the episcleral vein, the suprachoroidal space, and Schlemm's canal.

25. The method according to claim 22, wherein the inserting comprises inserting the system through the cornea.

26. The method according to claim 22, wherein the inserting comprises:
inserting into the cornea or the limbus of the eye a hollow shaft that is configured to hold the shunt; and
advancing the shaft transocularly across the anterior chamber of the eye until the subconjunctival space is reached.

27. The method according to claim 26, wherein the inserting is conducted without penetrating the conjunctiva.

28. The method according to claim 22, wherein the shunt is positioned adjacent the distal end of the shaft during the inserting.

29. The method according to claim 22, wherein the shaft distal end extends beyond the shunt distal portion during the inserting.

30. The method according to claim 22, wherein movement of the plunger and the shaft is driven by a slot-and-pin mechanism.

31. The method according to claim 30, wherein the slot-and-pin mechanism is configured with the shaft and the plunger each comprising coupling portions at respective proximal sections thereof, the plunger coupling portion comprising a pin extending radially therefrom and constraining movement of the plunger, the shaft coupling portion comprising a pin extending radially therefrom and constraining movement of the shaft.

32. The method according to claim 31, wherein the pins constrain movement of the shaft and the plunger such that the shaft and the plunger are longitudinally movable along the axis relative to the housing.

33. The method according to claim 31, wherein the pins constrain radial movement of the shaft and the plunger.

34. The method according to claim 33, wherein the pins are configured to contact an inner surface of the housing to maintain longitudinal alignments of the coupling portions of the shaft and the plunger along the axis.

35. The method according to claim 31, further comprising a plunger arm and a shaft arm, the plunger arm comprising a plunger hub slot configured to receive the plunger coupling portion for coupling the plunger to the plunger arm, the shaft arm comprising a shaft hub slot configured to receive the shaft coupling portion for coupling the shaft to the shaft arm.

36. The method according to claim 35, further comprising a plunger motor coupled to the plunger arm for longitudinally moving the plunger along the axis and a shaft motor coupled to the shaft arm for axially moving the shaft along the axis.

37. The method according to claim 22, wherein the advancing the plunger comprises driving the plunger movement by a motor.

38. The method according to claim 22, wherein the retracting the shaft comprises driving the shaft movement by a motor.

39. The method according to claim 22, wherein the advancing the plunger comprises manually driving the plunger movement.

40. The method according to claim 22, wherein the retracting the shaft comprises manually driving the shaft movement.

* * * * *